US008772270B2

(12) United States Patent
Shulman et al.

(10) Patent No.: US 8,772,270 B2
(45) Date of Patent: Jul. 8, 2014

(54) TREATMENT METHODS REQUIRING PHYTO-INGREDIENTS

(75) Inventors: Avidor Shulman, Kiryat Tivon (IL); Dori Pelled, Hod Hasharon (IL); Tzafra Cohen, Haifa (IL); Orly Farkash, Shimshit (IL)

(73) Assignee: Enzymotec Ltd., Migdal Haemeq (IL)

( * ) Notice: Subject to any disclaimer, the term of this patent is extended or adjusted under 35 U.S.C. 154(b) by 465 days.

(21) Appl. No.: 11/673,726

(22) Filed: Feb. 12, 2007

(65) Prior Publication Data

US 2007/0196440 A1 Aug. 23, 2007

Related U.S. Application Data

(63) Continuation-in-part of application No. PCT/IL2005/000861, filed on Aug. 10, 2005.

(30) Foreign Application Priority Data

Aug. 10, 2004 (IL) .......................................... 163447

(51) Int. Cl.
*A61K 31/56* (2006.01)
*A61K 47/00* (2006.01)
*A23D 9/013* (2006.01)
*A23L 1/30* (2006.01)

(52) U.S. Cl.
CPC ................................... *A23D 9/013* (2013.01); *A23L 1/3004* (2013.01)
USPC ............ 514/170; 514/169; 514/171; 424/439

(58) Field of Classification Search
None
See application file for complete search history.

(56) References Cited

U.S. PATENT DOCUMENTS

| | | |
|---|---|---|
| 4,064,236 A | 12/1977 | Dorn |
| 4,457,917 A | 7/1984 | Schaller |
| 4,639,435 A | 1/1987 | Fujii |
| 4,755,383 A | 7/1988 | Fujii |
| 4,863,860 A | 9/1989 | Halling |
| 4,900,549 A | 2/1990 | De |
| 5,164,372 A | 11/1992 | Matsuo |
| 5,298,246 A | 3/1994 | Yano |
| 5,354,900 A | 10/1994 | Matsuo |
| 5,418,219 A | 5/1995 | Ueda |
| 5,439,688 A | 8/1995 | Orsolini |
| 5,554,378 A | 9/1996 | Uda |
| 5,733,877 A | 3/1998 | Sato |
| 5,736,519 A | 4/1998 | Deigin |
| 5,843,499 A | 12/1998 | Moreau |
| 5,998,396 A | 12/1999 | Nakano et al. |
| 6,025,348 A | 2/2000 | Goto |
| 6,046,022 A | 4/2000 | Zhang et al. |
| 6,080,173 A | 6/2000 | Williamson |
| 6,087,353 A | 7/2000 | Stewart et al. |
| 6,106,886 A | 8/2000 | Van |
| 6,113,972 A | 9/2000 | Corliss et al. |
| 6,129,924 A | 10/2000 | Maurel |
| 6,129,945 A | 10/2000 | Awad et al. |
| 6,139,897 A | 10/2000 | Goto et al. |
| 6,184,397 B1 | 2/2001 | Roden et al. |
| 6,303,586 B1 | 10/2001 | McPeak et al. |
| 6,326,050 B1 | 12/2001 | Goto et al. |
| 6,365,211 B1 | 4/2002 | Corrigan |
| 6,589,588 B1 | 7/2003 | Wester |
| 6,605,452 B1 | 8/2003 | Basheer |
| 6,620,440 B1 | 9/2003 | Hsia |
| 6,667,068 B2 | 12/2003 | Smith |
| 6,713,118 B2 | 3/2004 | Nakajima et al. |
| 6,753,032 B1 | 6/2004 | Hirokawa |
| 6,844,021 B2 | 1/2005 | Koike et al. |
| 7,008,661 B2 | 3/2006 | Koike |
| 8,507,466 B2 | 8/2013 | Plat |
| 2001/0046548 A1 | 11/2001 | Berry |
| 2002/0016314 A1 | 2/2002 | Schersl |
| 2002/0025349 A1 | 2/2002 | Brindavanam et al. |
| 2002/0045000 A1 | 4/2002 | Nakajima et al. |
| 2002/0045773 A1 | 4/2002 | Ekblom |
| 2002/0132035 A1 | 9/2002 | Tamarkin et al. |
| 2003/0031758 A1* | 2/2003 | Koss et al. ...................... 426/72 |
| 2003/0108591 A1 | 6/2003 | Meijer |
| 2003/0133965 A1 | 7/2003 | Bruno et al. |
| 2003/0158257 A1 | 8/2003 | Hase et al. |

(Continued)

FOREIGN PATENT DOCUMENTS

| | | |
|---|---|---|
| AU | 2003209617 | 8/2003 |
| AU | 2003209617 B2 | 9/2003 |

(Continued)

OTHER PUBLICATIONS http://en.wikipedia.org/wiki/Docosahexaenoic_acid).*
http://en.wikipedia.org/wiki/Eicosapentaenoic_acid).*
Enzymotec Press Release, dated Apr. 23, 2003 "CardiaBeat (formerly MultOil) shows potential health benefits at in vitro study".*
Anonymous, Functional oil shows triple action against heart disease, Nutraingredients.com Europe, XP-002359318, Feb. 11, 2004, p. 1-2, Internet Article. URL: http://www.nutraingredients.com/news/ng.as?n=49812-functional-oil-shows.
Anonymous, Supplementing with enhanced phytosterols, Prepared Foods, XP-002359317, Apr. 2004, p. 1, Internet Article, URL: http://www.findarticles.com/p/articles/mi_m3289/is_4_173/ai_n5998862.

(Continued)

*Primary Examiner* — Robert A Wax
*Assistant Examiner* — Jeffrey T Palenik
(74) *Attorney, Agent, or Firm* — Fleit Gibbons Gutman Bonhini & Bianco PL; Martin Fleit; Paul D. Bianco

(57) ABSTRACT

The invention provides methods for treatment of conditions which require phytosterol therapy without adversely affecting the bioavailability of lipophilic vitamins or lipophilic drugs. The method includes administering a mixture of phytosterol ester(s) (PS-E) and 1,3-diglyceride(s) (DAG) dissolved in an edible oil or fat. The invention also provides a method of improving weight management and a method of treating metabolic conditions that result in overweight. Dietary nutrients, food supplements and food articles containing the mixture are also provided.

20 Claims, 5 Drawing Sheets

(56) References Cited

U.S. PATENT DOCUMENTS

| | | |
|---|---|---|
| 2003/0225160 A1 | 12/2003 | Geerlings |
| 2004/0105931 A1 | 6/2004 | Basheer |
| 2004/0219188 A1 | 11/2004 | Comer et al. |
| 2005/0032757 A1* | 2/2005 | Cho .................. 514/170 |
| 2005/0054621 A1 | 3/2005 | Gako-Golan |
| 2005/0148666 A1 | 7/2005 | Hase et al. |
| 2006/0052351 A1 | 3/2006 | Platt |
| 2006/0233862 A1 | 10/2006 | Alander |
| 2006/0233863 A1 | 10/2006 | Platt |
| 2009/0232916 A1 | 9/2009 | Shulman |
| 2010/0184734 A1 | 7/2010 | Plat et al. |

FOREIGN PATENT DOCUMENTS

| | | | |
|---|---|---|---|
| AU | 2003209617 | 9/2009 | |
| BG | 104701 A | 2/2002 | |
| BG | 104701 U | 2/2002 | |
| CA | 2279402 A1 | 9/1999 | |
| CA | 2375023 A1 | 12/2000 | |
| CH | 692263 | 9/1975 | |
| CH | 692263 A5 | 4/2002 | |
| CN | 1171106 A | 1/1998 | |
| CN | 1348983 A | 5/2002 | |
| DE | 3909707 A1 | 3/1989 | |
| DE | 3909707 A1 | 10/1989 | |
| EP | 0099039 A1 | 1/1984 | |
| EP | 0195311 A2 | 9/1986 | |
| EP | 0203706 A2 | 12/1986 | |
| EP | 0195311 | 6/1990 | |
| EP | 0982315 A2 | 3/2000 | |
| EP | 0990391 | 4/2000 | |
| EP | 1121928 A1 | 8/2001 | |
| EP | 1180545 A1 | 2/2002 | |
| FR | 2761887 A1 | 10/1998 | |
| GB | 1405346 | 9/1975 | |
| IL | WO 03/064444 | * 8/2003 | ............. C07J 9/00 |
| IL | WO 2004/069150 | * 8/2004 | |
| JP | 61293341 | 12/1986 | |
| JP | 61293341 A | 12/1986 | |
| JP | 2001040388 A | 2/2001 | |
| JP | 20010403388 A | 2/2001 | |
| JP | 2001247473 A | 9/2001 | |
| JP | 2002034453 A | 2/2002 | |
| JP | 2002138297 A | 5/2002 | |
| JP | 2002206100 A | 7/2002 | |
| JP | 2004201672 A | 7/2004 | |
| JP | 2004210652 A | 7/2004 | |
| JP | 2004519232 T | 7/2004 | |
| KR | 20010035226 A | 5/2001 | |
| RU | 2205004 C2 | 5/2003 | |
| WO | 9614311 | 5/1996 | |
| WO | 9904782 | 2/1999 | |
| WO | 9904782 A1 | 2/1999 | |
| WO | 9948378 | 2/1999 | |
| WO | 9913737 | 3/1999 | |
| WO | 9948378 A1 | 9/1999 | |
| WO | 9956558 | 11/1999 | |
| WO | 9959423 A1 | 11/1999 | |
| WO | WO 99/59423 | 11/1999 | |
| WO | 9963031 A1 | 12/1999 | |
| WO | 0019842 | 4/2000 | |
| WO | 0056869 | 9/2000 | |
| WO | 0073407 A1 | 12/2000 | |
| WO | 0115552 A1 | 3/2001 | |
| WO | 0132029 | 5/2001 | |
| WO | 0132029 A2 | 5/2001 | |
| WO | 0132035 A1 | 5/2001 | |
| WO | 0172136 A1 | 10/2001 | |
| WO | 0175083 A1 | 10/2001 | |
| WO | WO 02/11550 | 2/2002 | |
| WO | 02060272 | 8/2002 | |
| WO | 02060272 A1 | 8/2002 | |
| WO | 02100412 | 12/2002 | |
| WO | 02100412 A2 | 12/2002 | |
| WO | 03064444 A1 | 8/2003 | |
| WO | WO 03/064444 | 8/2003 | |
| WO | 2004069150 | 8/2004 | |
| WO | WO 2004/069150 | 8/2004 | |
| WO | 2006016363 | 2/2006 | |

OTHER PUBLICATIONS

Atif B. Awad et al., Phytosterols as Anticancer Dietary Components: Evidence and Mechanism of Action, Nutr. American Society for Nutritional Sciences, 2000, p. 2127-2130, v. 130.

Alvin Berger et al., Plant sterols: factors affecting their efficacy and safety as functional food ingredients, Lipids in Health and Disease, Apr. 7, 2004. pp. 1-19, v.3, No. 5.

Steven N. Blair et al., Incremental Reduction of Serum Total Cholesterol and Low-Density Lipoprotein Cholesterol With the Addition of Plant Stanol Ester-Containing Spread to Statin Therapy, The American Journal of Cardiology, Jul. 1, 2000, pp. 46-52, v. 86.

Patrick J.D. Bouic, The role of phytosterols and phytosterlins in inmmune modulation: a review of the past 10 years, Current Opinion in Clinical Nutrition and Metabolic Care, 2001, pp. 471-475. v. 4.

S. De Jongh et al., Plant sterols lower LDL cholesterol without improving endothelial function in prepubertal children with familiall hypercholesterolaemia, J. Inherit, Metab. Dis., 2003, pp. 343-351, v. 26.

Anonymous, Enzymotec launches health oil ingredient, Nutraceuticals International, XP009058643, Apr. 2003, pp. 24.

The PRIME Study Group prepared by J.W.G. Yarnell, The PRIME study: classical risk factors do not explain the severalfold differences in risk of coronary heart disease between France and Northern Ireland, Q J Med., 1998, pp. 567-676, v. 91.

Catherine M. Gordon, MD, MSc et al., Prevalence of Vitamin D Deficiency Among Health Adolescents, Arch Pediatr Adolesc Med, 2004, pp. 531-537, v. 158.

Helena Gylling et al., Cholesterol Reduction by Different Stanol Mixtures and With Variable Fat Intake, Metabolism, May 1999, pp. 575-580, V. 48, No. 5.

HFJ Hendriks et al., Spreads enriched with three different levels of vegetable oil sterols and the degree of cholesterol lowering in normocholesterolaemic and mildly hypercholesterolaemic subjects, European Journal of Clinical Nutrition, 1999, pp. 319-327, v. 53.

"ISSFAL", International Society for the Study of Fatty Acids and Lipids, ISSFAL Newsletter, XP-002359319, 2003, pp. 1-28, v. 10. No. 3.

A. Paul Jayaraj et al., Duodenal Ulcer Prevalence: Research into the Nature of Possible Protectice Dietary Lipids, Phytotherapy Research, 2003, pp. 391-398, v. 17.

International Search Rep for PCT/IL05/000861, Feb. 6, 2006.

Intl Prelim Exam Rep for PCT/IL05/000861, Jan. 8, 2007.

Written Opinion of the International Searching Authority for PCT/IL2005/000861.

Peter J.H. Jones et al., Dietary phytosterols as cholesterol-lowering agents in humans, Can. J. Physiol. Pharmacol., 1997, pp. 217-227, v. 75.

Martin B. Katan, PhD. et al., Efficacy and Safety of Plant Stanols and Sterols in the Management of Blood Cholesterol Levels, Mayo Clinic Proceedings, 2003, pp. 965-978, v. 78.

Vivian Wy Lau et al., Plant sterols are efficacious in lowering plasma LDL and non-HDL cholesterol in hypercholesterolemic type 2 diabetic and nondiabetic persons, Am. J. Clin. Nutr., 2005 pp. 1351-1358, v. 81.

Alice H. Lichtenstein et al., Stanol/Sterol Ester-Containing Foods and Blood Cholesterol Levels, Circulation, 2001, pp. 1177-1179, v. 103.

W.H. Ling et al., Dietary Phytosterols: A Review of Metabolism, Benefits and Side Effects, Life Science, 1995, pp. 195-206, v. 57, No. 3.

S. Meguro et al., Original Copomunication Solubilization of phytosterols in diacylglycerol versus triacylglycerol improves the serum cholesterol-lowering effect, European Journal of Clinical Nutrition, 2001, pp. 513-517, v. 55.

Robert A. Moreau et al., phytosterols, phytostanols, and their conjugates in foods: structural diversity, quantitative analysis, and jealth-promoting uses, Progress in Lipid Research, 2002, pp. 457-500, v. 41.

(56) References Cited

OTHER PUBLICATIONS

Marcus J. Mussner et al., Effects of Phytosterol Ester-Enriched Margarine on Plasma Lipoprotein in Mild to Moderate Hypercholesterolemia are related to Basal Cholesterol and Fat Intake, Metabolism, Feb. 2002, pp. 189-194, v. 51, No. 2.
Manny Noakes et al., An increase in dietary carotenoids when consuming plant sterols or stanols is effective in maintaining plasma carotenoid, Am. J. Nutr., 2002, pp. 79-86, v. 75.
Richard E. Ostlund Jr., Phytosterol and cholesterol metabolism, Current Opinion in Lipidology, 2004, pp. 37-41, v. 15.
Myriam Richelle et al., Both free and esterified plant sterols reduce cholesterol absorption and the bioavailability of beta-carotene and gama-tocopherol in normocholesterolemis humans, American Society for Clinical Nutrition, 2004, pp. 171-177, v. 80.
Leon A. Simons, MD., Additive Effect of Plant Sterol-Ester Margarine and Cerivastatin in Lowering Low-Density Lipoprotein Cholesterol in Primary Hypercholesterolemia. Oct. 1, 2002, The American Journal of Cardiology, pp. 737-740, v. 90.
Alpo F. Vuorio et al., Stand Ester Margarine Alone and With Sumvastatin Lowers Serum Cholesterol in Families With Familial Hypercholesterolemia Caused by the FH-North Karelia Mutation, Arterioscler Thromb Vasc Biol, 2000, pp. 500-506, v. 20.
M. Akhtar Javed et al., Fatty Acid and Lipid Composition of Sesamim Indicum DC, Pakistan Journal of Scientific and Industrial Research, XP009058587, Feb. 2000, pp. 23-25, v. 43. No. 1.
Hopkins, Garry J. et al, "Role of triglyceride-rich lipoproteins and hepatic lipase in determining the particle size and composition of high density lipoproteins", pp. 1265-1277, J. Lipid Res. 1986.
Horrobin, David F., "The Roles of Essential Fatty Acids in the Development of Diabetic Neuropathy and Other Complicatinos of Diabetes Mellitus", pp. 181-197, 1988, Prostaglandins Leukotrienes and Essential Fatty Acids.
Intensive blood-glucose control with sulphonylureas or insulin compared with conventional treatment and risk of complications in patients with type 2 diabetes (UKPDS 33) Lancet1998; pp. 837-853.
Jellema A. et al, "Weight reduction, but not a moderate intake of fish oil, lowers concentrations of inflammatory markers and PAI-1 antigen in obese men during the fasting and postprandial state" Eur J. Clin Invest 2004 pp. 766-773.
Johnston, Richard B. Jr., "Measurement of O2—Secreted by Monocytes1", Methods in Enzymology, vol. 105, pp. 365-269 (1984).
Jones, Peter JH et al, "Lipids in Health and disease" pp. 1-9, Oct. 25, 2007 BioMed Central Ltd.
Jousilahti, Pekka et al, "Serum Cholesterol Distribution and Coronary Heart Disease Risk" pp. 1087-1094, 1998 Americal Heart Association, Inc.
Kalman, R. et al, "The Efficiency or Sand Rat Metabolism is Responsible for Development of Obesity and Diabetes", Jan. 18, 1993, vol. 4 pp. 57-98.
Kaplan, Marielle et al, "Oxidized Low Density Lipoprotein: Atherogenic and Proinflammatory Characteristics during Macrophage Foam Cell Formation. An Inhibitory Role for Nutritional Antioxidants and Serum Paraoxonase", Clin Chem Lab Med, 1999 pp. 777-787.
Karpe, F., "Postprandial Lipoprotein metabolism and atherosclerosis", pp. 341-355, Journal of Internal Medicine 1999.
Katan, Martijn B. et al, "Efficacy and Safety of Plant Stanols and Sterols in the Management of Blood Cholesterol Levels" pp. 965-978, Mayo Clinic Proceedings: Aug. 2003.
Keidar, Shlomo, "Angiotensin, LDL Peroxidation and Atherosclerosis", Life Sciences, vol. 63, pp. 1-11, 1998.
Kris-Etherton, Penny M. PhD. et al, "Fish Consumption, Fish Oil, Omega-3 Fatty Acids, and Cardiovascular Disease", pp. 2747-2757, Circulation, 2002 American Heart Association, Inc.
Kondo, Akira et al, "Insulin Treatment Prevents LDL from Accelerated Oxidationin Patients with Diabetes", J. Atheroscler Thromb, 2002, pp. 280-287.
Krauss, Ronald M., MD., "Lipids and Lipoproteins in Patients With type 2 Diabetes", pp. 1496-1504, Diabetes Care 2004.
Kris-Etherton, Penny M. et al, "High-monounsaturated fatty acid diets lower both plasma cholesterol and triacylglycerol concentrations 1-3", Am. J. Clin Nutr 1999 pp. 1009-1015.
Laakso, Markku et al, "Adverse Effects of Obesity on Lipids and Lipoprotein Levels in Insulin-Dependent and Non-Insulin-Dependent Diabetes", Metabolism, vol. 39. 1990, pp. 117-122.
Larkin, Marilynn, "Diet and exercise delay onset of type 2 diabetes, say US experts", p. 565 vol. 358, Aug. 18, 2001.
Law, Malcolm, "Plant sterol and stanol margarines and health", pp. 861-864, BMJ2000.
Lemieux, Isabelle, et al "Total Cholesterol/HDL Cholesterol Ratio vs LDL Cholesterol/HDL Cholesterol Radio as Indices of Ischemic Heart Disease Risk in Men", arch Intern Med. 2001, pp. 2685-2692.
Ling, W.H. et al, "Dietary Phytosterols: A Review of Metabolism, Benefits and Side Effects", Life Sciences, vol. 57, pp. 195-206, 1995 XP-000995149.
Logroscino, Giancarlo et al, "Prospective study of type 2 diabetes and cognitive decline in women aged 80-81 years", pp. 1-6, Feb. 23, 2004 Papers.
Luo, Jing, et al, "Moderate Intake of n-3 Fatty Acids for 2 Months Has No Detrimental Effect on Glucose Metabolism and Could Ameliorate the Lipid Profile in Type 2 Diabetic Men", Diabetes Care vol. 21, May 1998, pp. 717-724.
Mackness, Bharti, PhD. et al, "Low Paraoxonase Activity Predicts Coronary Events in the Caerphilly Prospective Study", Circulation 2003, pp. 2775-27769.
Madigan, Claire et al, "Dietary Unsaturated Fatty Acids in Type 2 Diabetes", Diabetes Care 23, pp. 1472-1477, 2000.
Maki et al, Diacylglycerol Oil Consumption is an Effective Adjunct in Managing Obesity, p. A301, 2002.
Matsuzawa, Yuji et al, "Pathophysiology and Pathogenesis of Visceral Fat Obesity", pp. 399-406, 1990.
Montori, Victor M. MD., "Fish Oil Supplementation in Type 2 Diabetes", Diabetes Care, vol. 23, No. 9, Sep. 2000, pp. 1407-1415.
Moreau, Robert A. et al, "Phytosterols, phytostanols, and their conjugates in foods: structural diversity, quantitative analysis, and health-promoting uses", Progress in Lipid Research 41 (2002) 457-500, Progress in Lipid Research.
Mori, Trevor A. et al, "Purified eicosapentaenoic and docosahexaenoic acids have differential effects on serum lipids and lipoproteins, LDL particle size, glucose, and insulin in mildly hyperlipidemic men 1-3", Am J. Clin Nutr 2000 pp. 1085-1094.
Mori, Trevor et al, "Effect of Eicosapentaenoic Acid and Docosahexaenoic Acid on Oxidative Stress and Inflammatory Markers in Treated-Hypertensive Type 2 Diabetic Subjects",Free Radical Biology & medicine, vol. 35, No. 7, pp. 772-781, 2003.
Murase, Takatoshi et al, "Dietary diacylglycerol suppresses high fat and high sucrose diet-induced body fat accumulation in C57BL/6J mice", pp. 372-378, Journal of Lipid Research, vol. 42, 2001.
Murase, Takatoshi et al, "Anti-obesity effect of dietary diacylglycerol in C57BL/6J mice: dietary diacylglycerol stimulates intestinal lipid metabolism" pp. 1312-1319, J. Lipid Res. 2002.
Muskiet, Frits A. J. et al, "Is Docosahexaenoic Aid (DHA) Essential? Lessons from DHA Status Regulation, Our Ancient Diet, Epidemiology and Randomized Controlled Trials", pp. 183-186, American Society for Nutritional Sciences J. Nutr. 134, 2004.
Naghavi, Morteza et al, "From Vulnerable Plaque to Vulnerable Patient A Call for New Definitions and risk Assessment Strategies: Part I", pp. 1664-1672, 2003 American Heart Association, Inc.
Nissen, Steven E., et al, "Statin Therapy, LDL Cholesterol, C-Reactive Protein, and Coronary Artery Disease", pp. 29-38, N. England J. Med Jan. 6, 2005.
Normen, Lena et al, "Combination of Phytosterols and Omega-3 Fatty Acids: A Potential Strategy to Promote Cardiovascular Health", Curr, Med. Chem.—Cardiovascular & Hematological Agents, 2004, vol. 2, pp. 1-12.
Ohr, Linda Milo, Fats for Healthy Living, Nutraceuticals & Functional Foods, Jul. 2003, vol. 67, No. 7, pp. 91-96.
Pollak, O.J., M.D., Ph.D., "Reduction of Blood Cholesterol in Man", pp. 702-706, Circulation, May 1956.
Rajagopalan, Sanjay et al, "Angiotensin II—mediated Hypertension in the Rat Increases Vascular Superoxide Production via Membrane

(56) References Cited

OTHER PUBLICATIONS

NADH/NADPH Oxidase Activation", pp. 1916-1923, The Journal of Clinical Investigation, vol. 97, No. 8, Apr. 1996, 1916-1923.
Relimpio, F. et al, Relationships of apolipoprotein B100 with the metabolic syndrome in Type 2 diabetes mellitus, Diabetes Research and Clinical Practice 57 (2002), pp. 199-207.
Rifai, Nader et al, "Proposed Cardiovascular Risk Assessment Algorithm Using High-sensitivity C-Reactive Protein and Lipid Screening", pp. 28-30, Clinical chemistry 47, No. 1, 2001.
Risman, pp. 220-222. 1998.
Ross, Russell, "The pathogenesis of atherosclerosis: a perspective for the 1990s", pp. 801-809, Nature,vol. 362, Apr. 29, 1993.
Ruiz-Gutierrez, V. et al, "Cell membrane fatty acid composition in Type 1 (insulin-dependent) diabetic patients: relationship with sodium transport obnormalities and metabolic control", Diabetologia (1993) vol. 36, pp. 850-856.
Sanchez-Muniz, F.J. et al, "Small supplements of N-3 fatty acids a change serum low density lipoprotein composition by decreasing phospholipid and apolipoprotein B concentrations in young adult women", European Journal of Nutrition, vol. 38, pp. 20-27 (1999).
Sarkkinen, E. et al, "The effects of monounsaturated-fat enriched diet and polyunsaturated-fat enriched diet on lipid and glucose metabolism in subjects with impaired glucose tolerance", European Journal of Clinical nutrition (19976), vol. 50, pp. 595-598, dated 1996.
Schaffner, Thomas, et al, "Arterial Foam Cells With Distinctive Immunomorphologic and Histochemical Features of Macrophages", pp. 57-80, American Journal of Pathology 1980.
Shafrir, Eleazar et al, "Psammomys Obesus of the Jerusalem Colony: A Model for Nutritionally Induced, Non-Insulin-Dependent diabetes", 83-99, Mar. 24, 1993.
Sniderman, Allan D., "Hypertriglyceridemic HyperapoB: The Unappreciated Atherogenic Dyslipoproteinemia in Type 2 Diabetes Mellitus", pp. 447-459, 2001.
Souci, S. W. et al., "Food Composition and Nutrition Tables", pp. 12-14 XP-002354065, 2000.
Stark, Aliza H. et al., "Olive Oil as a Functional Food: Epidemiology and Nutritional Approaches", pp. 170-176, vol. 60, No. 6 Nutrition Reviews, dated Jun. 2002.
Steinberg, Daniel et al., "Beyond Cholesterol" Modifications of Low-Density Lipoprotein That Increase Its Atherogenicity, vol. 320, No. 14 1986.
Stone, Neil J. et al., "Summary of the Scientific Confernce on the Efficacy of Hypocholesterolemic Dietary Interventions", pp. 3388-3391, 1996 Americal Heart Assoc. Inc.
Tada, Norio, "Physiological actions of diacylglycerol outcome" pp. 145-149, Current Opinion in Clinical Nutrition and metabolic Are 2004.
Taguchi, Hiroyuki et al, "Energy Value and Digestibility of Dietary Oil Containing Mainly 1,3-Diacylglycerol Are Similar to Those of Triacylglycerol" pp. 379-382, Lipids, vol. 36, No. 4, 2001).
Taguchi, Hiroyuki, "Double-Blind Controlled Study on the Effects of Dietary Diacylglycerol on Postprandial Serum and Chylomicron Triacylglycerol Responses in Healthy Humans", Journal of the American College of Nutrition, vol. 19, No. 6,, pp. 789-796(2000).
Takase, Hideto PhD., "Metabolism of diacylglycerol in humans", Asia Pac J. Clin Nutr. 2007 pp. 398-403.
The Diabetes Prevention Program, pp. 623-634, Diabetes Care 1999.
Thomas, et al, "Free Radicals and Environmental Toxins" pp. 1075-1083, Annals of Emergency Medicine; 15(9); Sep. 1986.
Tilly-Kiesi, Marju et al, "Hyperinsulinemia and insulin resistance are associated with multiple abnormalities of lipoprotein subclasses in glucose-tolerant relatives of NIDDM patients" pp. 1569-1578, Journal of Lipid Research, vol. 37, 1996.
Tremblay, Andre, J. et al, "Associations Between the Fatty Acid Content of Triglyceride, Visceral Adipose Tissue Accumulation, and Components of the Insulin Resistance Syndrome", Metabolism, vol. 53, No. 3 Mar. 2004. pp. 310-317.
Tsimikas, Sotirious et al, "Oxidized Phospholipids, Lp(a) Lipoprotein, and Coronary Artery Disease" pp. 46-57, N. Engl. J. Med. 353, Jul. 7, 2005.
Tsuzura, S. et al, "Correlation of Plasma Oxidized Low-Density Lipoprotein Levels to Vascular Complications and Human Serum Paraoxonase in Patients With Type 2 Diabetes", pp. 297-302, Metabolism, vol. 53, No. 3 Mar. 2004.
UK Prospective Diabetes Study 16, "Overview of 6 Years' Therapy of Type II Diabetes: A Progressive Disease" pp. 1249-1258, Diabetes, vol. 44, Nov. 1995.
Vessby, B. et al, "Substituting dietary saturated for monounsaturated fat impairs insulin sensitivity in healthy men and women: the KANWU study", pp. 312-319, Diabetologia (2001).
Visioli, Francesco et al, "Low density lipoprotein oxidation is inhibited in vitro by olive oil constituents" pp. 25-32, Atherosclerosis 117 (1995).
Walldius G., et al, "Apolipoprotein B and apolipoprotein A-I: risk indicators of coronary heart disease and targets for lipid-modifying therapy", pp. 188-205, Journal of Internal Medicine 2004.
Wilt, T. et al Cernilton for benign prostatic hyperplasia,The Cochrane Library 2008.
XP-002354042, 2003.
XP-002354047, 2000.
XP-002354049, 2003.
XP-002242960, 2001 Database WPI Section ch, Week 200166.
Yanagitani, Yoshihiro et al, "Angiotension II Type 1 Receptor—Mediated Peroxide Production in Human Macrophages", Hypertension, pp. 335-339, 1999 American Heart Association, Inc.
Yorek, Mark A., "The Role of Oxidative Stress in Diabetic Vascular and Neural Disease", pp. 471-480, Free Radical Research, 2003, vol. 37.
Zimmet, Paul et al, "Global and societal implications of the diabetes epidemic", pp. 782-787, 2001 McMillan Magazines Ltd.
Ziv, Ehud et al, "*Psammomys obesus*: Primary Insulin Resistance Leading to Nutritionally Induced Type 2 Diabetes" pp. 327-342, 1996.
Miettinen,Tatu A. et al, "Reduction of Serum Cholesterol With Sitostanol-Ester Margarine in a Mildly hypercholesterolemic Population", The New England journal of Medicine, pp. 1308-1312, Nov. 16, 1995.
Nagao, Tomonori et al, "Dietary Diacylglycerol Suppresses Accumulation of Body Fat Compared to Triacylglycerol in Men in a Double-Blind Controlled Trial", J. Nutr. 130, pp. 792-797, 2000.
Mussner et al., "Effects of Phytosterol Ester-Enriched Margarine on Plasma Lipoproteins in Mild to Moderate Hypercholesterolemia Are Related to Basal Cholesterol and Fat Intake", pp. 189-194, XP-002267083, Metabolism, vol. 51, No. 2 Feb. 2002.
Meguro, S. "Original Communication Solubilization of phytosterols in diacylglycerol versus triacylglycerol improves the serum cholesterol-lowering effect", pp. 513-517, (2001), European Journal of Clinical Nutrition, XP009021731.
http://loowayup.com (notice of reference cited from Office Action dated Jul. 22, 2010).
http://www.diabetes.org (notice of reference cited from Office Action dated Jul. 22, 2010).
Ewart, Stephen H. et al, Fish Oil Containing Phytosterol Esters Alters Blood Lipid Profiles and Left Ventricle Generation of Thromboxane A2 in Adult Guinea Pigs 1,2, pp. 1149-1152, 2002, American Society for Nutritional Sciences.
Russell, James C. et al, "Improvement of Vascular Dysfunction and Blood Lipids of Insulin-Resistant Rats by a Marin Oil-Based Phytosterol Compound", pp. 147-152, Lipids, vol. 37, No. 2 (2002).
Awad, Atif et al, "Effect of β-Sitosterol, a Plant Sterol, on Growth, Protein Phosphatase 2A, and Phospholipase D in LNCaP Cells", Nutrition and Cancer, vol. 36(1), pp. 74-78, dated 2000.
Carreo, Juan J. et al, "Cardiovascular Effects of Milk Enriched With ω-3 Polyunsaturated Fatty Acids, Oleic Acid, Folic Acid, and Vitamins E and B6 in Volunteers With Mild Hyperlipidemia", XP-002354041, Nutrition 20:521-527, 2004.
Blum, Database FSTA Online, 2000, XP-002354043.
Demonty et al, "Fish-oil esters of plant sterols improve the lipid profile of dyslipidemic subjects more than do fish-oil or sunflower oil esters of plant sterols1-3", pp. 1534-1532, American Journal of Clinical Nutrition 2006.
Katan, Martijn et al "Beyond Low-Fat Diets", vol. 337, No. 8, pp. 563-566, National Medical Library, Aug. 30, 2005.

(56) References Cited

OTHER PUBLICATIONS

Logroscino, Giancarlo et al, "Prospective study of type 2 diabetes and cognitive decline in women aged 70-81 years", pp. 106, Feb. 2004, BMJ.
Mackness, Bharti, et al, "Low Paraoxonase Activity Predicts Coronary Events in the Caerphilly Phospective Study", pp. 2775-2779, Mar. 4, 2003, American Heart Association, Inc.
Maritim, A.C. et al, Diabetes, Oxidative Stress, and Antioxidants: A review, pp. 24-38, J. Biochem Molecular Toxicology, vol. 17, 2003.
For U.S. Appl. No. 11/199,584, Office Action dated Jul. 8, 2010; Office Action dated Oct. 14, 2009 and Office Action dated Mar. 18, 2009, Amendment filed Jun. 8, 2009, Amendment filed Apr. 14, 2010, Amendment filed Jan. 10, 2011.
For U.S. Appl. No. 11/573,457, Office Action dated Mar. 29, 2011, Office Action dated Jul. 22, 2010, and Office Action dated Feb. 18, 2010, Preliminary Amendment filed Feb. 9, 2007, Response to Election/Restriction filed Mar. 23, 2010, Amendment filed Jan. 24, 2011.
For U.S. Appl. No. 10/888,087, Office Action dated Aug. 24, 2009, Office Action dated Feb. 4, 2009, Office Action dated Jun. 11, 2008, Office Action dated Oct. 25, 2007, and Office Action dated Jul. 2, 2007, Response to Election/Restriction filed Aug. 1, 2007, Amendment filed Feb. 27, 2008, Amendment filed Sep. 11, 2008, Supplemental Response filed Oct. 30, 2008, Amendment filed Jun. 3, 2009, Amendment filed Dec. 23, 2009.
Kao Corp. "Oil and Fat for Food", JP2002034453A2, p. 1, Feb. 5, 2002, Abstract only.
Enzymotec launches healthy oil ingredient, Nutraceuticals International, Apr. 2003, p. 24.
Notice of Reasons of Rejection for JP2007-525450, Jul. 28, 2011.
Ewart et al., "Fish Oil Containing Phytosterol Esters Alters Blood Lipid Profiles and Left Ventricle Generation of Thromboxane A2 in Adult Guinea Pigs", Biochemical and Molecular Actions of Nutrients Research Communication, 2002, 132:1149-1152, American Society for Nutritional Sciences, Canada.
Harris, W.S., "Omega-3 long-chain PUFA and triglyceride lowering: minimum effective intakes", "European Heart Journal Supplements", 2001, 3:D59-D61, The European Society of Cardiology.
Kuksis, A and Beveridge J.M.R., "Preparation and Certain Physical Properties of Some Plant Steryl Esters", J. Org. Chem., 1960, 25:(7)1209-1219.
Pihlajamaki et al., "Insulin resistance is associated with increased cholesterol synthesis and decreased cholesterol absorption in normoglycemic men", Journal of Lipid Research, 2004, 45:507-512, American Society for Biochemistry and Molecular Biology.
Seki, S. et al., "Effects of phytosterol ester-enriched vegetable oil on plasma lipoproteins in healthy men", Asia Pacific Journal of Clinical Nutrition (2003) vol. 12, No. 3, pp. 282-291.
Flickinger, B.D. et al., "Nutritional characteristics of DAG oil", Lipids (2003) vol. 38, No. 2, pp. 129-132, AOCS Press.
"Enzymotec launches healthy oil", News article posted on Nutraungredients.com related to "Oil comprising PS-E and DAG" (Mar. 3, 2003).
"Functional oil shows triple action against heart disease", News article posted on Nutraungredients.com related to "Oil comprising PS-E and DAG" (Feb. 11, 2004).
International Preliminary Report on Patentability published May 23, 2007 for International Patent Application No. PCT/IL2005/000861 filed on Aug. 10, 2005.
Written Opinion (WO) published Feb. 10, 2007 for International Patent Application No. PCT/ IL2005/000861 filed on Aug. 10, 2005.
International Preliminary Report published May 23, 2007 for PCT/IL2005/000861, filed Aug. 10, 2005.
International Search Report published Mar. 16, 2006 for PCT/IL2005/000861, filed Aug. 10, 2005.
American diabetes "Nutrition Principles and recommendation in Diabetes" (2004), pp. 1-42.
Amundsen, Agot L. et al, Plant sterol ester-enriched spred lowers plasma total and LDL cholesterol in children with familial hypercholesterolemia 1,2, p. 338-344, Am J. Clin Nutr 2002.

Assman, Gerd et al, "Hypertriglyceridemia and Elevated Lipoprotein (a) Are Risk Factors for Major coronary Events in Middle-Aged Men", pp. 1179-1184, 1996 by Excerpta Media, Inc.
Austin, Melissa A. et al, "Hypertriglyceridemia as a Cardiovascular Risk Factor", pp. 7B-12B, 1998 by Excerpta medica, Inc.
Austin, Melissa A., "Plasma Triglyceride as a Risk Factor for Coronary Heart disease", pp. 249, vol. 129, No. 2 1989, American Journal of Epidemiology.
Aviram, Michael et al, "Dietary Olive Oil Reduces Low-Density Lipoprotein Uptake by Macrophages and Decreases the Susceptibility of the Lipoprotein to Undergo Lipid Peroxidation", pp. 75-84, Ann Nutr Metab 1993.
Aviram, Michael, "Modified forms of low density lipoprotein and atherosclerosis" pp. 1-9, Atherosclerosis, 98 (1993).
Aviram, Michael, "Oxidative Modification of Low Density Lipoprotein and Its Relation to Atherosclerosis", pp. 241-249, Israel Journal of Medical Sciences, vol. 31, 1995.
Aviram, Michael, "Macrophage Form Cell Formation During Early Atherogenesis Is Determined by the Balance Between pro-Oxidants and Anti-Oxidants in Arterial Cells and Blood Lipoproteins", pp. 585-594, Antioxidants & Redox Signaling, vol. 1, No. 4, 1999, Mary Ann Liebert, Inc.
Aviram, Michal, "Interaction of Oxidized Low Density Lipoprotein with Macrophages in Atherosclerosis, and the Antiatherogenicity of Antioxidants", pp. 599-608, Eur. J. Clin Chem Clin Biochem 1996.
Aviram, Michal, "Review of Human Studies on Oxidative Damage and Antioxidant Protection Related to Cardiovascular Diseases", pp. 85-97, vol. 33, Free Radical Research (Nov. 2000; 33 Suppl. S85-97.
Awad, Atif B. et al, "Phytosterols as Anticancer Dietary Components: Evidence and mechanism of Action 1,2" pp. 2127-2130, 2000 American Society for Nutritional Sciences.
Awad, A.B. et al, "Dietary Phytosterols Inhibits the Growth and metastasis of MDA-MD-231 Human Breast Cancer Cells Grown in SCID Mice", pp. 821-824, (2000), Anticancer Research.
Barr, David P. et al, "Protein-lipid Relationships in Human Plasma", pp. 480-493, Oct. 1951.
Baynes, John W. et al, "Role of Oxidative Stress in Diabetic Complications", pp. 1-9, Diabetes, vol. 48, Jan. 1999.
Belinky, Paula A., et al, "Structural Aspects of the Inhibitory Effect of Glabridin on LDL Oxidation", pp. 1419-1429, Free Radical Biology & Medicine, vol. 24, 1998.
Belinky, Paula A. et al, "The antioxidative effects of the isoflavan glabridin on endogenous constituents of LDL during its oxidation", pp. 49-61, Atherosclerosis 137, (1998).
Blonk, Marion C. et al, "Dose-response effects of fish-oil supplementation in healthy volunteers", pp. 120-127, Am J Clin Nutr 1990.
Brown, Michael S. et al, "Lipoprotein Metabolism in the Macrophage: Implications for cholesterol Deposition in Atherosclerosis1", pp. 223-261, Ann Rreview Biochem 1983.
Calabresi, Laura et al, "An ω-3 Polyunsaturated Fatty Acid Concentrate Increases Plasma High-Density Lipoprotein 2 Cholesterol and Paraoxonase Levels in Patients With Familial Combined Hyperlipidemia", pp. 153-158, Metabolism, vol. 53, No. 2 Feb. 2004.
Calder, Philip C., "n-3 Polyunsaturated Fatty Acids and Cytokine Production in Health and Disease", pp. 203-234, Am Nutr Metab 1997.
Perez-Camino, M.C., "Determination of diacylglycerol isomers in vegetable oils by solid-phase extraction followed by gas chromatography on a polar phase", pp. 305-314, Journal of Chromatography A, 721 (1996).
Ceconi, Claudio et al, "Oxidative stress in cardiovascular disease: myth or fact?, pp. 217-221, Archives of Biochemistry and Biophysics" 420 (2003).
Chisolm, Guy M. et al, "The Oxidative Modification Hypothesis of Atherogenesis an Overview", pp. 1815-1826, Free Radical Biology & Medicine, vol. 28, No. 12. 2000.
Conner, William et al, "Should a Low-Fat High-Carbohydrate Diet Be Recommended for Everyone?", pp. 562-563, Aug. 21, 1997, The New England Journal of Medicine.
Dr. Conner et al, "Rebuttals", pp. 566-567, Aug. 21, 1997, The New England Journal of Medicine.

(56) References Cited

OTHER PUBLICATIONS

Coste, Thierry, et al, "Neuroprotective Effect of Docosahexaenoic Acid-Enriched Phospholipids in Experimental Diabetic Neuropathy", pp. 25782585, 2003 Diabetes, vol. 52.

Danesh, John et al, "Lipoprotein(a) and Coronary Heart Disease Meta-Analysis of Prospective Studies" pp. 1082-1085, Circulation. 2000.

Davidson, Michael H. et al, Efects of Docosahexaenoic Acid on Serum Lipoproteins in Patients with Combined Hyperlipidemia: A Randomized, Double-Blind, Placebo-Controlled Trial, Journal of the Americal Collect of Nutrition, vol. 16, No. 3, pp. 236-243, (1997).

Naranjan S. Dhalla et al, "Role of oxidative stress in cardiovascular diseases", pp. 655-673, Journal of Hyrtension 2000.

Duckworth, William C. MD, "Hyperglycemia and Cardiovascular Disease", pp. 383-391, Current Atherosclerosis Reports 2001.

Dunstan, David W. et al, "The Independent and Combined Effects of Aerobic Exercise and Dietary Fish Intake on Serum Lipids and Glycemic Control in NIDDM", pp. 913-921, Diabetes Care, vol. 20, No. 6, Jun. 1997.

Expert Panel on Detection, Evaluation, and Treatment of High Blood Cholesterol in Adults, Executive Summary of the Third Report of the National Cholesterol Education Program (NCEP) Expert Panel on Detection, Evaluation, and Treatment of High Blood Cholesterol in Adults (Adult Treatment Panel III), pp. 2486-2497, JAMA, May 16, 2001, vol. 285.

Fasching P. et al, "Fish Oil Supplementation Versus Gemfibrozil Treatment in Hyperlipidemic NIDDM", Horm. Metab. Res. 28 (1996) pp. 230-236.

Franz, Marion J. et al, "Evidence-Based Nutrition Principles and Recommendations for the Treatment and Prevention of Diabetes and Related Complications", pp. 148-198, Diabetes Care, vol. 25, Jan. 2002.

Gaullier, Jean-Michel et al, "Conjugated linoleic acid supplementation for 1 y reduces body fat mass in healthy overweight humans 1-3", Am. J. Clin Nutr 2004, pp. 1118-1125.

Gerbi, Alain et al, "Fish Oil Supplementaton Prevents Diabetes-Induced Nerve Conduction Velocity and Neuroanatomical Changes in Rats 1-2", pp. 207-213, 1999, American Society for Nutritional Sciences.

Gerrity, Ross G. Phd., "The Role of the Monocyte in Atherogenesis", pp. 181-190, Am J. Pathol 1981.

Glass, Christopher K. et al, "Atherosclerosis: The Road Ahead", pp. 503-516, Cell, vol. 104, 503-516, Feb. 23, 2001.

Goupy, Pascale et al, "Quantitative Kinetic Analysis of Hydrogen Transfer Reactions from Dietary Polyphenols to the DPPH Radical", J. Agric. Food Chem 2003, 51, 615-622.

Griendling, Kathy K., PhD et al, Oxidative Stress and Cardiovascular Injury Part II: Animal and Human Studies, pp. 2034-2040, Circulation 2003, American Heart Association, Inc.

Grundy, Scott M., "Obesity, Metabolic Syndrome, and Cardiovascular Disease", pp. 2595-2600, The Journal of Clinical Endocrinology & Metabolism 2004.

Hallikainen, Maarit A. et al, "Plant Stenol Esters Affect Serum Cholesterol Concentrations of Hypercholesterolemic Men and Women in a Dose-dependent Manner", pp. 767-776, 2000 American Society for Nutritional Sciences.

Hansen, John-Bjarne et al, "Effects of Highly Purified Eicosapentaenoic Acid and Docosahexaenoic Acid on Fatty Acid Absorption, Incorporation into Serum Phospholipids and Postprandial triglyceridemia", pp. 131-138, 1998, Lipids.

Harris, William S. et al, "Effects of Four Doses of n-3 Fatty Acids given to Hyperlipidemic Patients for Six Months" pp. 220-227 (1991) John Wiley & Sons, Inc.

Haisma, Hinke et al, "Complementary Feeding with Cow's Milk Alters Sleeping Metabolic rate in Breast-Fed Infants 1,2", pp. 189-1895, 2005 American Society for Nutritional Sciences.

Hayes, Charlotte, "Diabetes Bars and Beverages: The Benefits and the Controversies", pp. 11-14, Diabetes Spectrum, vol. 15, 2002.

Heinecke, Jay W., MD, "Oxidative Stress: New Approaches to Diagnosis and Prognosis in Atherosclerosis", pp. 12A-16A, 2003 Am J. Cardiol.

Brassica Juncea (L.) Szern. "Low Erucic Acid Rapeseed Oil" Oct. 22, 1999, pp. 1-24, GRAS.

Spencer, "Fatty Acid Composition as a Basis for Identification of Commercial Fats and Oils" vol. 53, No. 3 pp. 94-96, Journal of the American Oil Chemists' Society, dated 1976.

Office Action mailed Jun. 10, 2013 for U.S. Appl. No. 10/886,087, filed Jul. 9, 2004.

Jones et al, "Fish-oil esters of plant sterols differ from vegetable-oil sterol esters in triglycerides lowering, carotenoid bioavailability and impact on plasminogen activator inhibitor-1 (PAI-1) concentrations in hypercholesterolemic subjects", pp. 1-9, Oct. 25, 2007, Lipids in Health and Disease.

For U.S. Appl. No. 10/888,087, Office Action dated Aug. 24, 2009, Office Action dated Feb. 4, 2009, Office Action dated Jun. 11, 2008, Office Action dated Oct. 25, 2007, and Office Action dated Jul. 2, 2007, Response to Election/Restriction filed Aug. 1, 2007, Amendment filed Feb. 27, 2008, Amendment filed Sep. 11, 2008, Supplemental Response filed Oct. 30, 2008, Amendment filed Jun. 3, 2009, Amendment.

For U.S. Appl. No. 10/888,087, Office Action dated Jul. 2, 2007, Jun. 10, 2013, Response with terminal disclaimer filed Dec. 10, 2013, Interview summary dated Dec. 11, 2013.

Awad et al., Nutr. Cancer, 2000, pp. 74-78, vol. 36.

Davidson MH, Maki KC, Kalkowski J, Schaefer EJ, Torri SA, Drennan KB, Effects of docosahexaenoic acid on serum lipoproteins in patients with combined hyperlipidemia: a randomized, double-blind, placebo-controlled trial. J Am Coll Nutr. Jun. 1997;16(3):236-43.

Laasko et al., Metabolism, 1990, pp. 117-122, vol. 39.

Lou et al., Diabetes Care, 1998, pp. 717-724, vol. 21.

Wilt et al., Cochrane Database Syst. Rev., 1998, vol. 3, Art. No. CD001042 DOI:10.1002/14651858.CD001042.

Austin M.A. (1989) Am. J. Epidemiol. 129: 249-259.

Aviram M. (2000) Free. Radic. Res. 33: S85-97.

Ceconi, C. et al. (2003) Arch. Biochem. Biophys. 420: 217-221.

Chisolm G.M. and Steinberg D. (2000) Free Radic. Biol. Med. 28: 1815-1826.

Connor W.E. and Connor S.L. (1997) N. Engl. J. Med. 337: 562-563.

Gerrity R.G. (1981) Am. J. Pathol. 103: 181-190.

Steinberg D. et al. (1989) N. Engl. J. Med. 320: 915-924.

Thomas C.E. and Aust. S.D. (1986) Ann. Emerg. Med. 15(9): 1075-83.

Tsuzura, S. et al. (2004) Metabolism 53: 297-302.

Walldius J. and Junger I. (2004) J. Intern. Med. 255: 188-205.

Yorek M.A. (2003) Free Radic. Res. 37: 471-80.

International Search Report for PCT/IL2004/000131 filed Feb. 10, 2004.

International Preliminary Report on Patentability for PCT/IL2004/000131 filed Feb. 10, 2004.

Office Action issued Jun. 23, 2009 in connection with U.S. Appl. No. 11/396,257, filed Mar. 31, 2006.

For U.S. Appl. No. 12/655,240: Office Actions dated Oct. 11, 2011; Feb. 1, 2012; Oct. 24, 2012; Responses dated Nov. 10, 2011; Aug. 1, 2012; Jan. 24, 2013; Mar. 11, 2013; Inteview Summary dated Mar. 19, 2013; NOA dated Apr. 10, 2013.

XP009058643; Enzymotec Press Release. Apr. 23, 2003.

Kim et al. XP-002242960; Preparation method Fat oil composition containing high content. Jan. 18, 2011.

International Preliminary Examination Report issued Jan. 10, 2007 in connection with PCT International Application No. PCT/IL2005/000861.

International Search Report issued dated Feb. 6, 2006 in connection PCT International Application No. PCT/IL2005/000861.

http://lookwayup.com. Jun. 15, 2010.

Vuorio AF, Gylling H, Turtola H, Kontula K, Ketonen P, Miettinen TA. Stanol ester margarine alone and with simvastatin lowers serum cholesterol in families with familial hypercholesterolemia caused by the FH-North Karelia mutation. Arterioscler Thromb Vasc Biol. Feb. 2000;20(2):500-6.

(56) References Cited

OTHER PUBLICATIONS

Database FSTA Online! International Food Information Service (IFIS), Frankfurt-Main, DE; 2003, Blum M: 'Vitamins, carotenoids and PUFA: key factors for functional foods.' XP002354043.
Jones PJ, Demonty I, Chan YM, Herzog Y, Pelled D. Fish-oil esters of plant sterols differ from vegetable-oil sterol esters in triglycerides lowering, carotenoid bioavailability and impact on plasminogen activator inhibitor-I(PAI-1) concentrations in hypercholesterolemic subjects. Lipids Health Dis. Oct. 25, 2007;6:28.
Logroscino G, Kang JH, Grodstein F. Prospective study of type 2 diabetes and cognitive decline in women aged 70-81 years. BMJ. Mar. 6, 2004;328(7439) :548-553.
XP-0020354042; Nutritional Facts of Peanuts in the Diet Part 2. Nutrition and Food Science. 2003; 33(2): 56-64.
XP-002354047; Potential Health Benefits of Flax Seed. 1999.
Fu Z, Hou Y, Jiang T. XP-0020354049; Nutrient Health Food Function Reduce Blood Fat Delay Senile Preparation Process. Nutrition and Food Science. 2002.
'Enzymotec launches healthy oil' Nutraingredients.com; Mar. 2, 2003.
MacDonald R, Ishani A, Rutks I, Wilt TJ. A systematic review of Cernilton for the treatment of benign prostatic hyperplasia. BJU Int. May 2000;85(7):1-36. Review.
http://en.Wikipedia.org/wiki/docosahexaeoic_acid. Nov. 17, 2009.
http://en.Wikipedia.org/wiki/eicosaoentaenoic_acid. Nov. 17, 2009.
http://diabetes.org. Jul. 2, 2010.
For U.S. Appl. No. 11/199,584 Office Action dated Oct. 9, 2013.
For U.S. Appl. No. 11/396,257 Office Action dated Jun. 23, 2009; notice of abandonment dated Jan. 6, 2010.
Database WPI Section Ch, Week 200166 Derwent Publications Ltd., London, GB; AN 2001-587540 XP002242960 & KR 2001 035 226 A (Onbio Corp), May 7, 2001.
Written Opinon received Aug. 2004 for PCT/IL04/131 filed Feb. 10, 2004.
XP-002359318;Functional Oil shows Triple Action Against Heart Disease; Nov. 2, 2004.
Maki et al Faseb J 15 (4) A301.
Pollak OJ. Reduction of blood cholesterol in man. Circulation. May 1953;7 (5):702-6.
XP 002359317; Prepared Foods: Supplementing with Enhanced Phyosterols; Apr. 2004.
Connor. "The New England Journal of Medicines", Aug. 21, 1997.
Duckworth, W., "Hyperglycemia and Cardiovascular Diseases", Apr. 18, 1995, pp. 1-9.
Fashing, P, et al. "Fish Oil Supplementation Versus Gemfibrozil Treatment in Hyperlipidemic: NIDDM", Apr. 18, 1995, pp. 230-360.
Kaplan, M, et al. "Oxidized Low Density Lipoprotein", 1999, pp. 777-787, Clin Chem Lab Med.
Katan M.B. et al. "Clinical Debate" 1999, pp. 1-4, Massachusetts Medical Society, vol. 337.
Keidar, S, "Angiotensin, LDL Peroxidation and Atherosclerosis". vol. 63 No. 1, 1998, pp. 1-11, Life Sciences.
Kondo, A. et al "Insulin Treatment Prevents LDL from Accelerated Oxidation in Patients with Diabetes", vol. 9, No. 6 , pp. 1-8,Jun. 14, 2002.
Etherton, Kris "High-monounsaturated fatty acid diets lower both plasma cholesterol and triacylglycerol concentrations", Abstract, pp. 1009-1500, Jul. 19, 1999. American J Clinical Nutrition.
Miettinen, T et al. "Reduction of Serum Cholesterol with Sitostanol-Ester Margarine in a Mildly Hypercholesterolemic Population", Journal, pp. 1308-1313, Nov. 16, 1995. The New England Journal of Medicine.
Murase, T et al. "Dietary diacylglycerol suppresses high fat and high sucrose diet-induced body gat accumulation in C57BL/6J mice", vol. 42 ,pp. 1-7. 2001, Journal of Lipid Research.
Rifai, N. et al. "Proposed Cardiovascular Risk Assessment Algorithm Using High-Sensitivity C-Reactive Protein and Lipid Screening", Clinical Chemistry 47, No. 1, (2001).
Sanchez-Muniz, et al. "Small supplement of N-3 fatty acids change serum low density lipoproein composition by decreasing phospholipid and apolipoprotein B concentrations in young adult women", pp. 20-27, 1999, European Journal of Nutrition.
Shafrir, E et al. "*Psammomys obesus* of the Jerusalem Colony", pp. 1-9, Mar. 24, 1993.
Taguchi, H et al. "Energy Value and Digestibility of Dietary Oil Containing Mainly 1,3- Diacyiglycerol are Similar to Those of Triacylglycerol", Lipids, vol. 26, No. 4 (2001).
Taguchi, H et al. "Double-Blind Controlled Study on the Effects of Dietary Diacylglycerol on Postprandial Serum and Chylomicron Triacylglycerol Responses in Healthy Humans", vol. 19, No. 6 (2000), Journal of American College of Nutrition, pp. 789-796.
Wikipedia, the free encyclopedia "Docosahexaenoic acid", Nov. 17, 2009.
Wikipedia, the free encyclopedia "Eicosapentaenoic acid", Nov. 17, 2009.
"Genetics of Diabetes", Jul. 2, 2010, Am Diabetes Assoc.
Visioli, F "International Society for the Study of Fatty Acids and Lipids", Issfal Newsletter, pp. 1-28, vol. 10 No. 3, published Winter 2003.

* cited by examiner

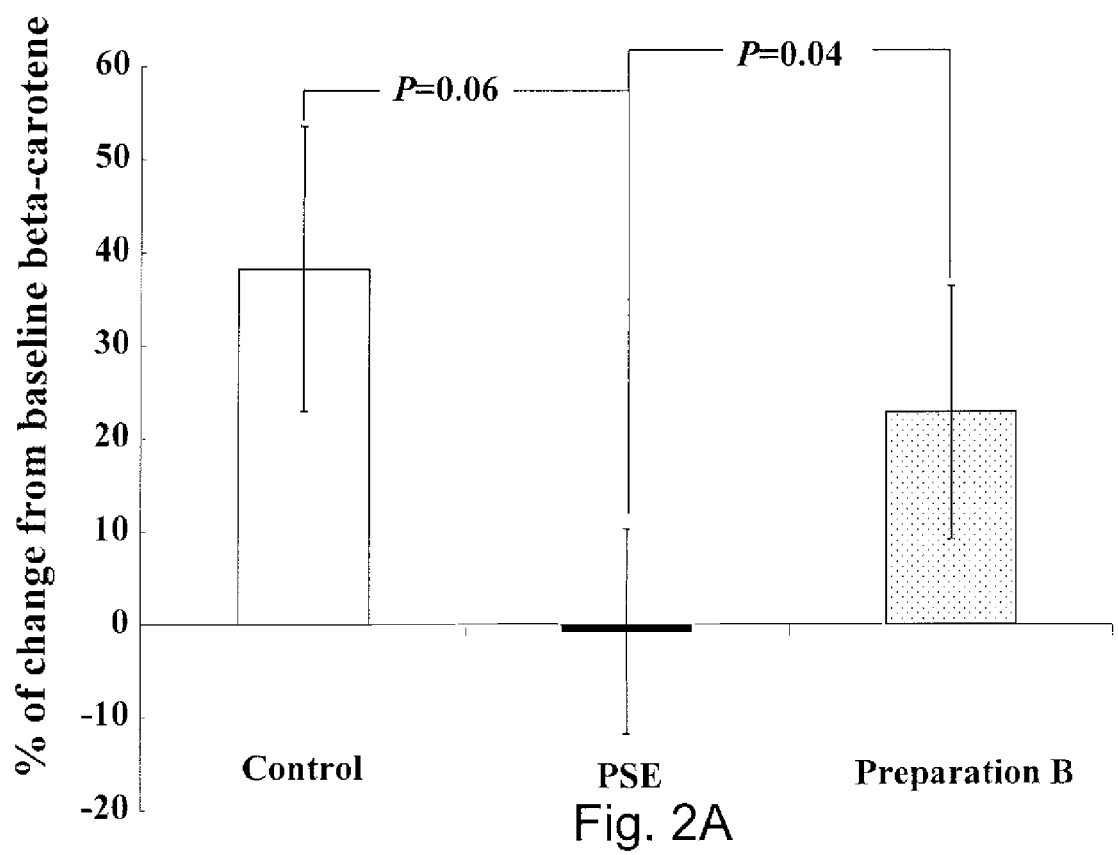

TREATMENT METHODS REQUIRING PHYTO-INGREDIENTS

CROSS-REFERENCE TO RELATED APPLICATION

This application is a continuation-in-part of the U.S. national stage designation of co-pending International Patent Application PCT/IL2005/000861, filed Aug. 10, 2005, the entire content of which is expressly incorporated herein by reference thereto.

FIELD OF THE INVENTION

The present invention refers to the field of functional foods and supplements in the treatment of medical conditions. More specifically, the present invention relates to the treatment of conditions with lipid mixtures containing phytosterols.

BACKGROUND OF THE INVENTION

All publications mentioned throughout this application are fully incorporated herein by reference, including all references cited therein.

Plant sterols are naturally occurring substances present in the diet as minor components of vegetable oils. Plant sterols have a role in plants similar to that of cholesterol in mammals, e.g. forming cell membrane structures. In human nutrition, both plant sterols and plant stanols are effective in lowering total plasma cholesterol and LDL-cholesterol levels. The term "phytosterols" covers plant sterols and plant stanols.

Phytosterols are components of a normal diet, mainly coming from plant sources, e.g. vegetable oils, seeds, nuts and grain-based products. The typical consumption of plant sterols in Western diets ranges between 200 and 400 mg/d, whereas the intake of phytostanols, the saturated form of plant sterols, is negligible.

The consumption of higher amounts of plant sterols and plant stanols lowers blood cholesterol levels by inhibiting the absorption of dietary and endogenously-produced cholesterol from the small intestine. This inhibition is related to the similarity in physico-chemical properties of plant sterols and stanols to cholesterol.

The plant sterols/stanols are very poorly absorbable compounds. Studies on the absorption, distribution, metabolism and excretion have shown that plant sterols are poorly absorbed from the intestine (1-10%).

The hypocholesterolemic action of phytosterols has been recognized since the early 1950's [Jones et al. (1997) *Can. J. Physiol. Pharmacol.* 75, 217-227]. The blood cholesterol-lowering effect of plant sterols has been investigated in a large number of clinical trials involving over 2,400 subjects, using doses as high as 25 grams per day for durations as long as three years. No significant adverse effects have been observed throughout the decades of medically supervised clinical efficacy testing or the general clinical use of plant sterols. Furthermore, the drug Cytellin (primarily β-sitosterol) was prescribed for more than 20 years and had an excellent safety record. In addition, both plant sterols and plant stanols have been subjected to rigorous toxicological evaluation.

Phytosterols or phytostanols, as well as their fatty acid esters and other derivatives, are common products provided as dietary supplements or as functional ingredients in a variety of health promoting foods and beverages, as well as dietary supplements, all in the aim of reducing blood levels of total cholesterol, and especially of LDL (low density lipoprotein) cholesterol.

Hypercholesterolemia (high blood cholesterol), which can be treated or controlled by phytosterols, is a major risk factor of cardiovascular disorders (CVD). CVD is one of the leading causes of mortality worldwide. Hypercholesterolemia also causes the formation and accumulation of plaque deposits in the arteries, which results in atherosclerosis, the pathological process underlying coronary heart disease (CHD), which is one kind of cardiovascular disorders.

Type 2 diabetes and also the associated conditions known as diabesity and metabolic syndrome, are related to CVD, whose incidence has also dramatically increased over the last century. In most cases, cardiovascular disorders are enhanced and even triggered by such metabolic disorders or their onset and development is accelerated by said syndromes. These are also closely related to risk factors of abnormal blood lipid profile, especially high levels of total cholesterol and non-HDL cholesterol species, mainly LDL cholesterol.

People at risk to develop a metabolic syndrome, diabetes, or obesity, as well as CVD or CHD, or that are already classified as patients of said conditions are cautioned to monitor and control their blood lipids profile, especially high levels of blood cholesterol. One of the most efficient methods to address this risk factor common to so many health conditions and risks is the ingestion of plant sterols or stanols or their derivatives.

A potent method of treatment that has been used to address such risk factor was the supplementation of both statins and phytosterols. Both active ingredients address high levels of blood cholesterol, each using a different mechanism of action. The pharmaceutical ingredients based on statins inhibit the de novo synthesis of cholesterol, while phytosterols inhibit the absorption of dietary and endogenously-produced cholesterol. It has been demonstrated that consumption of plant stanol esters by patients taking statin therapy but that still have elevated LDL-cholesterol levels, was able to further reduce the total and LDL cholesterol levels by up to 12% and 17%, respectively [Blair et al. (2000) *Am. J. Cardiol.* 86, 46-52]. In addition, treating subjects with primary hypercholesterolemia with statins and phytosterol-ester containing foods produced a purely additive effect on LDL cholesterol, reduction [Simons et al. (2002) *Am. J. Cardiol.* 90, 737-740]. In fact, Simons et al. have concluded that the addition of phytosterol-esters to statins therapy offers an LDL cholesterol reduction equivalent to doubling the dose of statins. Similar results were exhibited by others [Vuorio et al. (2000) *Arterioscler. Thromb. Vasc. Biol.* 500-506].

Post-menopausal females demonstrate several typical symptoms, like hot flashes, night sweats, sleeplessness, vaginal dryness, and disorders such as osteoporosis, CVD and central nervous system related alterations (anxiety and mood swings, depression and cognitive decline). With regards to the CVD complications in this population, it is well established that the rate of myocardial infarction increases by 3 fold and that cerebrovascular disease rises rapidly. It is believed that estrogen plays role in protecting endothelial cell wall and possibly protecting against thrombosis, hence the aforementioned symptoms following its deficiency. Hormone replacement therapy (HRT) has a clear role in the treatment of menopausal symptoms and osteoporosis. However, recent findings from Women Health Initiative (WHI) showed that taking HRT increases a woman's risk for heart disease, stroke, and pulmonary embolism. Recently, postmenopausal women (aged 50-55) consuming margarine-containing plant stanols for 6 weeks demonstrated a marked reduction of LDL cholesterol versus baseline, while HDL-cholesterol levels were increased, so the LDL/HDL cholesterol ratio was reduced [Gylling and Miettinen (1999) *Metabolism* 48:575-580].

However, following the different stanol interventions there was a notable decrease in □- and □-carotene concentrations while retinal, vitamin D and lipid standardized □-tocopherol levels were comparable to baseline values.

Phytosterols have also been connected and shown to have anti-cancer effects. Epidemiologic and experimental studies suggest that dietary phytosterols may offer protection from the most common cancers in Western societies, such as colon, breast and prostate cancer. Populations at low breast cancer risk consume more dietary phytosterols than those at high risk. Several in vitro studies have suggested that phytosterols are toxic to human breast cancer and prostate cancer cells. In vivo animal experiments have demonstrated the inhibitory effect of phytosterols on the incidence, growth and metastasis of colon tumors, breast, and prostate cancer [Awad, A. B. and Fink C. S. (2000) *J. Nutr.* 130:2127-2130; Moreaua, R. A. et al. (2002) *Progress in Lipid Research* 41:457-500]. Although there is evidence that phytosterols have anti-carcinogenic properties, the mechanism by which they inhibit tumor growth is not yet known. However, possible mechanisms by which phytosterols offer this protection include direct effect on membrane structure and function of tumor and host tissue, signal transduction pathways that regulate tumor growth and apoptosis [Awad and Fink (2000) id ibid].

One of the major risk factors to CVD and CHD, as well as of metabolic disorders such as diabetes type 2, is oxidative stress, a relative increase in free radicals. These are responsible, for example, for the increased formation of oxidized-LDL, which when found at relatively high levels, is responsible to the formation of foam cells, the hallmark of early atherosclerosis. Free radicals may be found at high levels in the blood and other tissues due to a variety of causes, some environmental, such as increased pollution, or related to poor nutrition, due to ingestion of pro-oxidative nutrients, or to insufficient ingestion of different anti-oxidative nutrients. In addition, elevated free radicals levels are common in metabolic conditions such as type 2 diabetes, diabesity and metabolic syndrome, accompanied with sustained blood hyperglycemic state. Oxidative stress can be treated or may be even prevented by a variety of active ingredients possessing anti-oxidative activity, basically neutralizing free radicals found in the body.

Phytosterols could have a possible role in prevention of inflammation-related conditions or disorders, including lymphocyte proliferative responses, pulmonary tuberculosis, human immunodeficiency virus (HIV), stress-induced immune suppression, rheumatoid arthritis, and allergic rhinitis/sinusitis [Bouic (2001) *Opin Clin Nutr. Metab. Care* 4:471-475]. The mechanisms by which plant sterols display their anti-inflammatory activity are thought to include inhibition of secretion of inflammatory mediators such as interleukin-6, and tumor necrosis factor-□ by monocytes; however most of the work has been conducted using animals models and therefore the specific mechanism remain to be elucidated.

Phytosterols also present anti-ulcer activity, protecting against *Helicobacter pylori* infection. In a recent study, phytosterol esters, but not sterols, in horse gram (an herb in the genus *Dolichos* cultivated in India for food and fodder) were protective in a pyloric ligation model of ulcer [Jayaraj et al. (2003) *Phytother Res* 17:391-398]. Together with sterols and phospholipids, these food lipids in diets may account for the low prevalence of duodenal ulcer in certain geographical areas, despite a uniformly high prevalence of *Helicobacter pylori* infection.

Any treatment addressing said disorders and/or conditions needs to be accompanied by a healthy and balanced nutrition. This nutrition should of course provide the patient with all the essential nutrients, among these vitamins. Many of the vitamins are lipophilic, and among those important to such patients are beta-carotene, vitamin A, vitamin D and vitamin E. These vitamins also possess anti-oxidative activity which is important to protect the body from oxidative stress and perhaps prevent the damages of free radical activities. Beta carotene is one of the most important and abundant of the carotenes, a portion of which the liver converts to vitamin A. Beta carotene is a powerful antioxidant with properties that can contribute to reducing cancer and heart disease. It's found in carrots and many colorful vegetables. Vitamin A, also known as retinol, is a carotenoid vitamin (see Scheme 1). Vitamin A is produced in the liver from different provitamin carotenoids, especially from beta-carotene, the most important provitamin A, and an anti-oxidant in itself. Vitamin D is acquired from the diet or produced in the skin and is biologically inactive. It must be metabolized by the liver to produce the 25-hydroxyvitamin D (25-OH-D). However, this compound is also biologically inactive under physiological conditions and must be activated by the kidney to produce the final vitamin D hormone, 1,25-dihydroxyvitamin D3. This hormonal form of vitamin D is important in calcium metabolism to form strong bones and teeth and prevent rickets, osteomalacia and osteoporosis. Vitamin E, also known as alpha-tocopherol, is mainly found in plant sources, and is also a potent anti-oxidant. This lipophilic vitamin is usually accompanied by other derivatives of the tocopherols skeleton, such as beta and gamma tocopherols.

While phytosterols and phytostanols, and their fatty acid esters, are one of the most efficient methods of treatment of the hypercholesterolemia risk factor, either alone or in combination with statins or other ingredients, recent studies have shown that the use of these phyto-ingredients may cause adverse effects. The primary concern regarding phytosterol supplementation is the effect it may have on the absorption and circulating levels of lipid soluble vitamins and carotenoids. Dietary phytosterols inhibit the absorption of dietary and biliary cholesterol, which in turn decreases the absorption of carotenoids and lipid soluble vitamins [Noakes et al. (2002) *Am. J. Clin. Nutr.* 75(1):79-86]. This presents a concern because, as mentioned above, there are many health benefits associated with dietary consumption of carotenoids and vitamins [Hendriks et al. (1999) *Eur. J. Clin. Nutr.* 53(4): 319-327].

Moreover, several clinical trials were identified in which the consumption of phytosterols was reported to induce a significant decrease in plasma carotenoid levels [Katan et al. (2003) *Mayo Clin. Proc.* 78(8): 965-978]. These decreases followed the consumption of spread or oils containing between 0.83 and 3.6 g phytosterols/day for periods of 3 to 52 weeks. Recently, the bioavailability of beta-carotene and alpha-tocopherol was reported to decrease in mildly overweight male volunteers following the consumption of 2.2 g phytosterols/day for a year [Richelle et al. (2004) *Am J. Clin. Nutr.* 80(1):171-177]. However, in this trial, plant sterol esters reduced the bioavailability of beta-carotene and alpha-tocopherol more than free plant sterols did. The reduction in beta-carotene levels was as high as 50%. Although conventional phytosterol esters (esterified with n-6 polyunsaturated fatty acids, such as soybean oil and sunflower oil fatty acids) are inferior to free phytosterols in their effect on vitamin absorption, they have the advantage of increased solubility, which is important for the process of phytosterol incorporation into micelles and inhibition of cholesterol absorption [Ostlund R E, Jr. (2004) Phytosterols and cholesterol metabolism. *Curr Opin Lipidol* 15, 37-41].

In addition, while the beneficial effect of phytosterol and statins combination therapy was demonstrated [Vuorio (2000) id ibid.], monitoring the blood levels of vitamin A, vitamin E, as well as of alpha- and beta-carotene, revealed that this treatment has resulted in reduction of serum levels of all vitamins and pro-vitamins, ranging from 10 to 50%. These effects were especially pronounced in children undergoing treatment due to a genetic condition [see review in Berger et al. (2004) *Lipids Health Dis.* 3:5-24].

The European Union Scientific Committee on Food (SCF) has concluded that marketing of foods containing phytosterols should be accompanied by an investigation of possible adverse health effects, including among others the effects on plasma beta-carotene levels. The UK Food Advisory Committee (FAC) has recommended that consumers should be informed that phytosterol ester-containing products are not nutritionally appropriate for young children and breast feeding women as they do not need to reduce their blood cholesterol levels and there is a possibility of affecting vitamin A levels. The Scientific Panel on Dietetic Products, Nutrition and Allergies of the European Food Safety Authority (EFSA) has emphasized the need for risk management measures in order to minimize the likelihood of a daily intake exceeding 3 g phytosterols/phytostanols, the provision of appropriate information to consumers regarding the need for regular consumption of fruits and vegetables to address the potential beta-carotene lowering effect of the product.

Lichtenstein and colleagues [Lichtenstein et al. (2001) *Circulation*. 103: 1177-1179] have pointed potential risks associated with the use of plant stanol/sterol ester-containing fats, among them observations of decreased levels of alpha and beta carotene, alpha-tocopherol, and/or lycopene in the plasma, as a result of the consumption of foods containing both stanol esters and sterol esters.

Since food products containing plant sterols are likely to be shared during meals by all family members, the potential for intake by non-hypercholesterolemic individuals is significant. Thus, the American Heart Association recommended that further studies and large-scale monitoring be undertaken to determine the long-term safety of plant sterol/stanol ester-containing foods in both normocholesterolemic and hypercholesterolemic adults, as well as in children.

As with adverse interactions between pharmaceutical active ingredients, the same should be avoided between different active ingredients or nutrients, either pharmaceutical or dietary, that may be utilized or that are required to address the health needs of CVD and other health conditions as described above. Such interactions may reduce the effectiveness or intake of one or more of the ingredients used in the treatment. On some cases, the interaction of the ingredients used in the treatment of said conditions may cause the reduction of the effectiveness or intake of other dietary nutrients or ingredients, needed by the individual to maintain his general health and to be able to cope with the specific risk factors for which he is being treated for. In general, the observed adverse effect of phytosterol administration on the intake of vitamin A and beta-carotene, as well as of vitamin E and D, may also be relevant to other dietary nutrients, active pharmaceutical ingredients or dietary active ingredients which are lipophilic as the carotenoids and tocopherols. Such lipophilic dietary nutrients, active pharmaceutical ingredients or dietary active ingredients that their intake or effectiveness may be further compromised by parallel administration of phytosterols include pharmaceutical anti-dyslipidemia ingredients, natural anti-oxidants, nutritional or active lipids, etc. Schemes 1 and 2 exemplify the chemical structure of several lipophilic active ingredients and dietary nutrients as well as of vitamin A and E.

Scheme 1 - Chemical structures of vitamins A, E and other lipophilic active ingredients and dietary nutrients

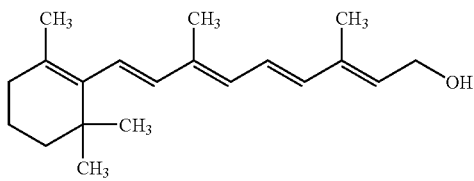

Vitamin A (Retinol)

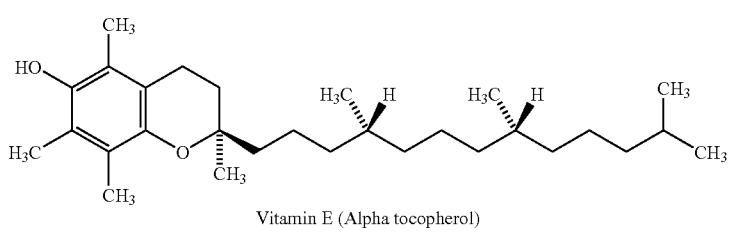

Vitamin E (Alpha tocopherol)

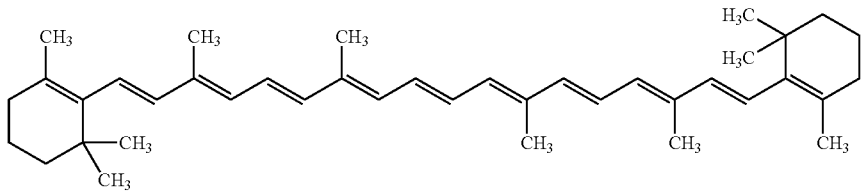

Beta-carotene

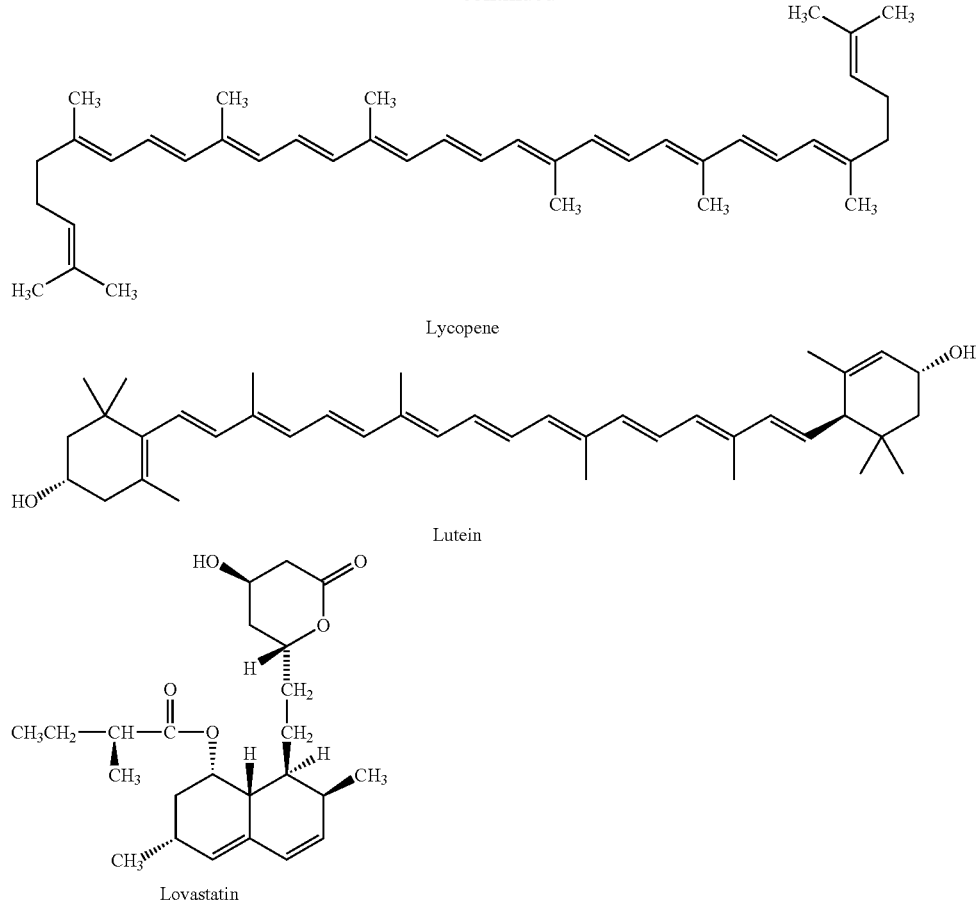

Lycopene

Lutein

Lovastatin

Scheme 2 - Chemical structure of the lipophilic omega-3 LC-PUFA DHA

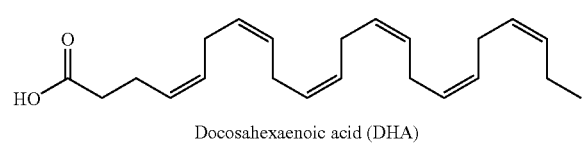

Docosahexaenoic acid (DHA)

Pharmaceutically active ingredients have been developed with the goal of controlling high levels of blood cholesterol, and are widely used in the treatment of populations at risk regarding the above described conditions. Perhaps the most popular approach relies on active ingredients of the statins chemical family, known to inhibit the biosynthetic pathway of cholesterol production, hence leading to lower levels of blood cholesterol levels. Other active ingredients used are bile acid-binding resins, cholesterol absorption inhibitors, combination cholesterol absorption inhibitors and statins, fibrates, and niacin.

A variety of synthetic anti-oxidants have been used for industrial and food purposes. Current methodology prefers the utilization of natural anti-oxidants, mainly derived from phyto-sources. Such plant derived anti-oxidants include lycopene, mainly found in red plants, especially tomatoes, and lutein. Other phyto-originated anti-oxidants include zeaxanthin and beta-carotene. All these anti-oxidants can be classified as highly lipophilic, which is a direct result of their common carotenoidic skeleton. Other anti-oxidants include those of the polyphenolic chemical characteristics. Such carotenoid, polyphenolic and other lipophilic natural anti-oxidants are all useful in the treatment of the above described conditions and their parallel administration to phytosterols should be beneficial.

Omega-3 long chain poly-unsaturated fatty acids (LC-PUFA), especially docosahexaenoic acid (DHA) and eicosapentaenoic acid (EPA) have been recognized as promoting cardiovascular health, partly due to the anti-hypertriglyceridemia activity. The US Food and Drug Administration (FDA) has announced on September 2004 that these fatty acids have earned a qualified health claim for the reduction of the risk of CHD by consumption of EPA- and DHA-containing foods or dietary supplements. Indeed, the consumption of these fatty acids can be beneficial to the populations suffering from the disorders or conditions discussed above or to populations wishing to prevent or inhibit the onset of said conditions.

All these ingredients, as well as others, may be used, in combination or alone, in order to address the risk factors of CVD, CHD, metabolic disordered patients, high risk populations, cancer patients, etc.

Other lipophilic pharmaceutical active ingredients, as well as other lipophilic dietary supplements, mainly phyto-ingredients extracted or derived from different plant sources, are to be found or are under development to address different health conditions which require or may benefit from parallel administration or intake of phytosterols and/or their derivatives, and hence face the risk of their intake being compromised by phytosterol administration, as mentioned above.

Therefore, in light of the beneficial effects of phytosterols as a method of treatment of, for example, hypercholesterolemia, or, in combination with additional ingredients addressing a variety of CVD, CHD, metabolic disorders-associated health risks, including hypertriglyceridemia, hyperglycemia and oxidative stress, as well as other health conditions, such as, inter alia, cancer and immune deficiency-associated diseases as detailed below, it is a purpose of the invention to provide a method of treatment that will enable making the most of the beneficial effects of phytosterols/phytostanols and their esters, without the possible adverse effects of inhibition of intake of other important ingredients such as vitamins, anti-oxidants and also lipophilic pharmaceutical active ingredients.

Overweight or obesity substantially increases the risk of morbidity from a number of conditions, including type 2 diabetes mellitus (DM), hypertension, dyslipidemia, coronary heart disease, congestive heart failure, stroke, gallbladder disease, hepatic steatosis, osteoarthritis, sleep apnea, and endometrial, breast, prostate, and colon cancers. An increase in all-cause mortality is also associated with higher body weights. Many of these conditions can be treated or prevented by the use of phytosterols/phytostanols and their esters.

It is a further purpose of the invention to provide a method of treatment providing the beneficial effects of phytosterols/phytostanols and their esters on hypercholesterolemia while also controlling, and even promoting a reduction in a patient's body weight.

Thus, it is an object of the present invention to provide a method of treatment for conditions which require phytosterol therapy without adversely affecting the bioavailability of any one of lipophilic vitamins, lipophilic drugs, lipophilic nutrients, or any lipophilic pharmaceutically active ingredient, through the administration of a mixture of PS-E (phytosterol ester(s)) and DAG (mainly 1,3 diglyceride(s)), dissolved or dispersed in an edible oil or fat, or a composition or food article comprising the same, to a subject in need.

It is a particular object of the present invention to provide a method for increasing and/or maintaining the bioavailability and patient's serum levels of lipophilic vitamins, lipophilic drugs, lipophilic nutrients, or lipophilic pharmaceutically active ingredients, in a subject in need of phytosterol therapy through the administration of a mixture of PS-E (phytosterol ester(s)) and DAG (mainly 1,3 diglyceride(s)), dissolved or dispersed in an edible oil or fat, or a composition or food article comprising the same.

It is a further object of the present invention to provide a method for delivering phytosterol to a subject in need without adversely affecting the bioavailability of lipophilic substances such as lipophilic vitamins, lipophilic drugs, lipophilic nutrients, or any lipophilic pharmaceutically active ingredient increasing and/or maintaining the bioavailability and patient's serum levels of lipophilic vitamins, lipophilic drugs, lipophilic nutrients, or lipophilic pharmaceutically active ingredients, and with even increasing the serum level of said lipophilic substance, through the administration of a mixture of PS-E (phytosterol ester(s)) and DAG (mainly 1,3 diglyceride(s)), dissolved or dispersed in an edible oil or fat, or a composition or food article comprising the same.

It is a further object of this invention to provide a platform for the delivery of phytosterol and/or derivatives thereof to a subject without adversely affecting the bioavailability of lipophilic vitamins or other essential nutrients and drugs, as was known for conventional phytosterol preparations.

These and other objects of the invention will become apparent as the description proceeds.

SUMMARY OF THE INVENTION

In a first aspect, the present invention provides a method of treating a condition which requires phytosterol therapy without adversely affecting the bioavailability of any one of lipophilic vitamins, lipophilic drugs, lipophilic nutrients, or any lipophilic pharmaceutically active ingredient, said method comprising administering a therapeutically effective amount of a mixture of PS-E (phytosterol ester(s)) and DAG (mainly 1,3 diglyceride(s)) (hereafter the composition of the invention), optionally dissolved or dispersed in an edible oil or fat, or a composition or food article comprising the same, to a subject in need.

In particular, the invention relates to a method of increasing or maintaining the bioavailability of any one of lipophilic vitamins, lipophilic drugs, lipophilic nutrients, or a lipophilic pharmaceutically active ingredient in a patient in need of phytosterol therapy, said method comprising administering a therapeutically effective amount of the composition of the invention, optionally dissolved or dispersed in an edible oil or fat, or a composition or food article comprising the same, to a subject in need.

The invention also relates to a method of delivering phytosterol to a patient in need of phytosterol therapy without adversely affecting the bioavailability of any one of lipophilic vitamins, lipophilic drugs, lipophilic nutrients, or a lipophilic pharmaceutically active ingredient, said method comprising administering a therapeutically effective amount of the composition of the invention, optionally dissolved or dispersed in an edible oil or fat, or a composition or food article comprising the same.

Preferably, the composition of the invention is dissolved or dispersed in an edible oil or fat, or a composition or food article comprising the same to a subject in need.

In one specific embodiment of the method of the invention, said lipophilic vitamins are carotenoids and tocopherols, preferably vitamin A and vitamin E, respectively. The lipophilic vitamin may also be vitamin D.

In another specific embodiment of the method of the invention, said lipophilic active ingredient is phytosterol(s).

In particular, the said patient in need of phytosterol therapy suffers from deficiencies in fat-soluble vitamins. Such deficiencies in fat-soluble vitamins may result from at least one of inappropriate diet, metabolic disorder, fats malabsorption, drug-vitamin direct or indirect interactions and impaired vitamin absorption.

The said patient may also suffer from a condition selected from the group consisting of cancer, benign prostatic hypertrophy, organ transplant, ulcer, prostatitis, cardiovascular disorder (CVD), coronary heart disease (CHD), atherosclerosis, pulmonary tuberculosis, human immunodeficiency virus (HIV), stress-induced immune suppression, rheumatoid arthritis, patients receiving any treatment resulting in immunosuppression, autoimmune patients, radiation-treated patients, chemotherapy-treated patients, and allergic rhinitis/sinusitis.

Patients in need of phytosterol therapy that suffer from an immune deficiency include patients suffering from human immunodeficiency virus (HIV), stress-induced immune suppression, rheumatoid arthritis, patients receiving any treatment resulting in immunosuppression, autoimmune patients, radiation-treated patients, chemotherapy-treated patients, and allergic rhinitis/sinusitis. In particular cases, said immunodeficiency is accompanied by increase in serum cholesterol levels.

Another particular group of patient is the population of elderly or geriatric patients, especially those suffering from at least one of age-associated vitamin D deficiency, age-associated hyperparathyroidism, calcium malabsorption, osteopenia and osteoporosis, weakness and falls.

A further group is the young population of children and adolescents, who may suffer in particular from vitamin D deficiency.

Deficiencies in fat-soluble vitamins due to diet, metabolic disorders, fats malabsorption, drug-vitamin interactions or due to impaired vitamin absorption could result in stroke, diabetes, breast cancer, immune deficiency, immune suppression, osteoporosis, osteopenia, photo-aging, skin tumor, photosensitivity reaction, cataractogenesis and cataracts, retinal photodeterioration, erythrocyte photochemolysis, photoerythema, photocarcinogenesis, Crohn's disease, short bowel syndrome, Alzheimer's disease, dementia, infantile nonalcoholic steatohepatitis and multiple sclerosis In another aspect, the present invention provides a method of improving weight management, comprising administering a therapeutically effective amount of a mixture of PS-E and DAG (mainly 1,3-diglyceride(s)), optionally dissolved or dispersed in an edible oil or fat, or a composition or food article comprising thereof, to a subject in need.

In a further aspect the present invention provides a method of treating a metabolic condition that results in overweight, comprising administering a therapeutically effective amount of a mixture of PS-E and DAG (mainly 1,3-diglyceride(s)) optionally dissolved or dispersed in an edible oil or fat, or a composition or food article comprising thereof, to a subject in need. In particular, said condition is obesity.

In one embodiment of the methods of the invention, said edible oil is selected from the group consisting of olive oil, fish oil, canola oil, soybean oil, sunflower oil, safflower oil, palm oil, avocado oil, sesame oil, flaxseed oil, and borage oil. Preferably, said oil is fish oil.

In another embodiment of the methods of the invention, said edible fat is any natural fat, selected from the group consisting of butter fat, anhydrous milk fat, cocoa butter and lard.

In a further embodiment of the methods of the invention, the fatty acid residues of the PS-E and of the DAG optionally correspond to the fatty acid residues of the oil from which it is derived, such as oleic, palmitic, palmitoleic, stearic, linoleic, linolenic, and eicosanoic, docosahexaenoic (DHA) and eicosapentaenoic (EPA) acid residues.

In another further embodiment of the methods of the invention, said phytosterol ester(s) is/are fatty acid ester(s) of stigmasterol, sitosterol, beta-sitosterol, brassicasterol, campesterol and/or 5-avenasterol and isomers and derivatives thereof and said phytostanol ester(s) is/are fatty acid ester(s) of beta-sitostanol, campestanol and/or stigmastanol and isomers and derivatives thereof.

In an even further embodiment of the methods of the invention, said mixture further comprises conventional ingredients of nutritional compositions.

In one particular embodiment of the methods of the invention, the weight ratio between phytosterol and/or phytostanol esters and diacylglycerol(s) and phytosterol and/or phytostanol ester(s) in said mixture is from about 15:1 to 1:1, preferably about 10:1 to about 1:1, more preferably 5:1 to 1:1 and particularly about 2:1.

In another particular embodiment of the methods of the invention, the amount of diacylglycerol(s) in said mixture is at least 1 wt %. More specifically, the amount of diacylglycerol(s) in said mixture is from about 1 to about 99 wt %, preferably from about 4 to about 70 wt %, particularly from about 7 to about 48 wt %, more particularly from about 1.0 to about 22 wt % and the amount of phytosterol and/or phytostanol ester(s) in said mixture is from about 1 to about 99 wt %, preferably from about 5 to about 70 wt %, more particularly from about 7 to about 60 wt %, specifically from about 10 to about 60 wt %, more particularly from about 7 to about 35 wt % and more specifically from about 20 to about 35 wt %.

In a further particular embodiment of the methods of the invention, the amount of phytosterol and/or phytostanol ester(s) in said mixture is at least 1 wt %.

In one preferred embodiment of the methods of the invention, said mixture consists of 15 wt % DAG, mainly 1,3-DAG(s) and 25 wt % total PS-E(s) dissolved or dispersed in one of olive, canola and fish oil.

In one specific aspect, the invention provides a method of improving weight management in women, comprising administering a therapeutically effective amount of a mixture of PS-E and DAG (mainly 1,3-diglyceride(s)), optionally dissolved or dispersed in olive oil, or a composition or food article comprising thereof, to a subject in need.

In a further aspect, the present invention provides a dietary nutrient, food supplement or food article comprising the composition of the invention, optionally dissolved or dispersed in an edible oil or fat, for treating conditions requiring phytosterol therapy which does not adversely affect, and even increases the bioavailability of any one of lipophilic vitamins, lipophilic drugs, lipophilic nutrients, or any lipophilic pharmaceutically active ingredient.

In one embodiment of the dietary nutrient or food supplement of the invention, said oil may be selected from the group consisting of olive oil, fish oil, canola oil, soybean oil, sunflower oil, safflower oil, palm oil, avocado oil, sesame oil, flaxseed oil, and borage oil. Preferably, said oil is fish oil.

In another embodiment of the dietary nutrient or food supplement of the invention, said edible fat may be any natural fat, selected from the group consisting of butter fat, anhydrous milk fat, cocoa butter and lard.

In a further embodiment of the dietary nutrient or food supplement of the invention, the fatty acid residues of the PS-E and of the DAG optionally correspond to the fatty acid residues of the oil from which it is derived, such as oleic, palmitic, palmitoleic, stearic, linoleic, linolenic, eicosanoic, docosahexaenoic (DHA) and eicosapentaenoic (EPA) acid residues. Oleic acids and LC-PUFA, including DHA and EPA are preferred.

In another further embodiment of the dietary nutrient or food supplement of the invention, the phytosterol ester(s) is/are fatty acid ester(s) of stigmasterol, sitosterol, beta-sitosterol, brassicasterol, campesterol and/or 5-avenasterol and isomers and derivatives thereof and said phytostanol ester(s) is/are fatty acid ester(s) of beta-sitostanol, campestanol and/or stigmastanol and isomers and derivatives thereof.

In an even further embodiment of the dietary nutrient or food supplement of the invention, said mixture further comprises conventional ingredients of nutritional compositions.

In one preferred embodiment of the dietary nutrient or food supplement of the invention, the weight ratio between phytosterol and/or phytostanol esters and diacylglycerol(s) and phytosterol and/or phytostanol ester(s) in said mixture is from about 15:1 to 1:1, preferably about 10:1 to about 1:1, more preferably 5:1 to 1:1 and particularly about 2:1.

In another preferred embodiment of the dietary nutrient or food supplement of the invention, the amount of diacylglycerol(s) in said mixture is at least 1 wt %.

More specifically, the amount of diacylglycerol(s) in said mixture is from about 1 to about 99 wt %, preferably from about 4 to about 70 wt %, particularly from about 7 to about 48 wt %, more particularly from about 10 to about 22 wt % and the amount of phytosterol and/or phytostanol ester(s) in said mixture is from about 1 to about 99 wt %, preferably from about 5 to about 70 wt %, more particularly from about 7 to about 60 wt %, specifically from about 10 to about 60 wt %, more particularly from about 7 to about 35 wt % and more specifically from about 20 to about 35 wt %.

In further preferred embodiment of the dietary nutrient or food supplement of the invention, the amount of phytosterol and/or phytostanol ester(s) in said mixture is at least 1 wt %.

Lastly, in the most preferred embodiment of the dietary nutrient or food supplement of the invention, said mixture consists of 15 wt % DAG, mainly 1,3-DAG(s) and 25 wt % total PS-E(s) dissolved or dispersed in one of olive, canola and fish oil.

The histogram represents the percentage of change of the levels of plasma vitamin A in subjects treated with PS-E alone or with PS-E+DAG-fish (Preparation A), in comparison with treatment with olive oil (control). Abbreviations. chan., change; cont., control; ol. o., olive oil; med., median; val., value; Prep. A, Preparation A.

FIG. 2A: % of Change of β-carotene plasma levels in subjects supplemented with control diet, preparation B, or PS-E.

Hypercholesterolemic overweight volunteers (n=5·7) were fed for four weeks with control diet (open bar), PS-E+DAG-olive (Preparation B) (dotted bar), or PS-E (closed bar), followed by four weeks of washout and counter supplementation. Beta-carotene levels were measured at the beginning and termination of each phase, as described in methods.

Figure 2B:
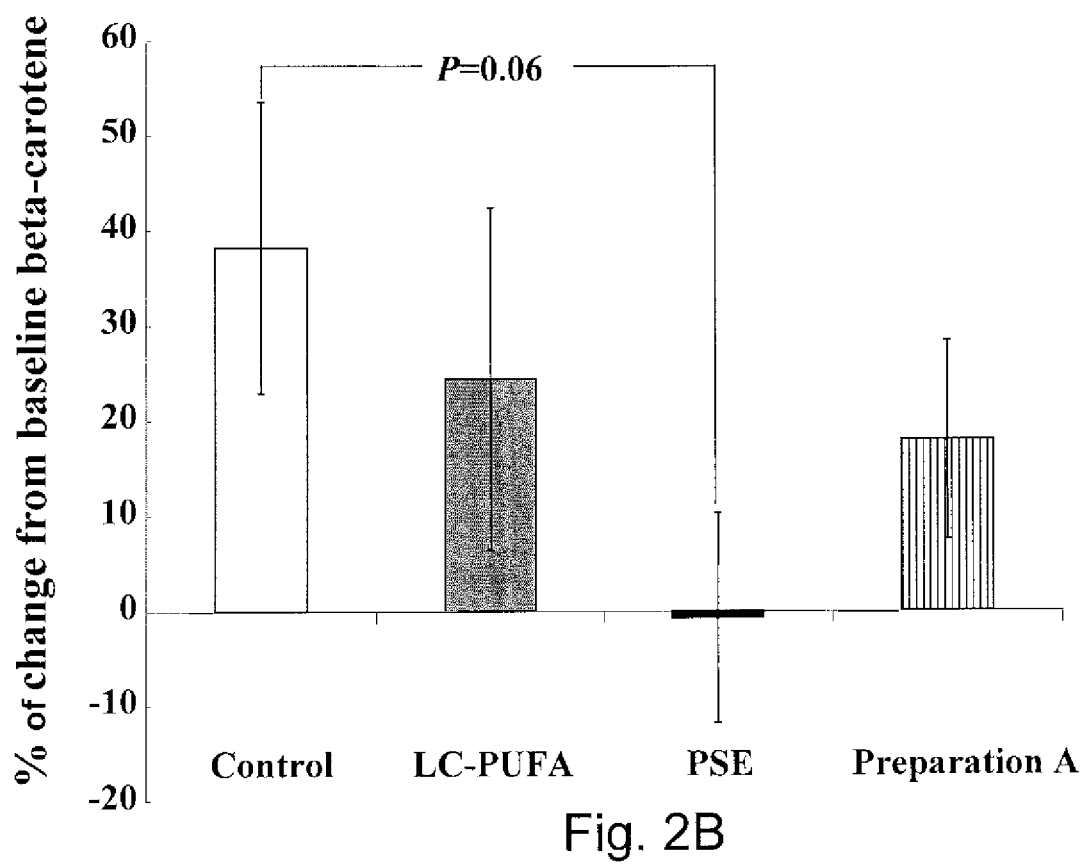

FIG. 2B: % of Change of β-carotene plasma levels of subjects supplemented with control diet, LC-PUFA, preparation A, or PS-E.

Hypercholesterolemic overweight volunteers (n=5–7) were fed for four weeks with control diet (open bar), LC-PUFA (gray bar), PS-E+DAG-fish (Preparation A) (striped bar) or PS-E (closed bar), followed by four weeks of washout and counter supplementation. Beta-carotene levels were measured at the beginning and termination of each phase, as described in methods.

Figure 3:
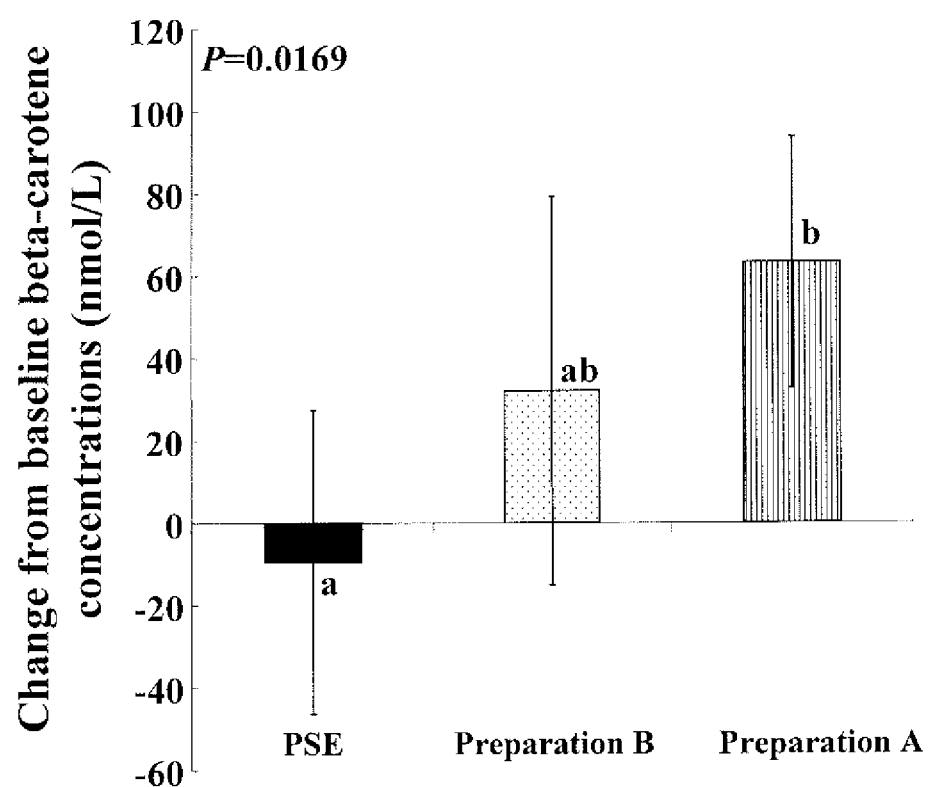

FIG. 3: Change of β-carotene plasma levels of subjects supplemented with PS matrices esterified with fatty acid originating from different sources Hypercholesterolemic overweight volunteers (n=21) were fed for four weeks with (Preparation A) (striped bar), PS-E+DAG-olive (Preparation B) (dotted bar), or PS-E (closed bar), followed by four weeks of washout and counter supplementation. Beta-carotene levels were measured at the beginning and termination of each phase, as described in methods.

Figure 4:
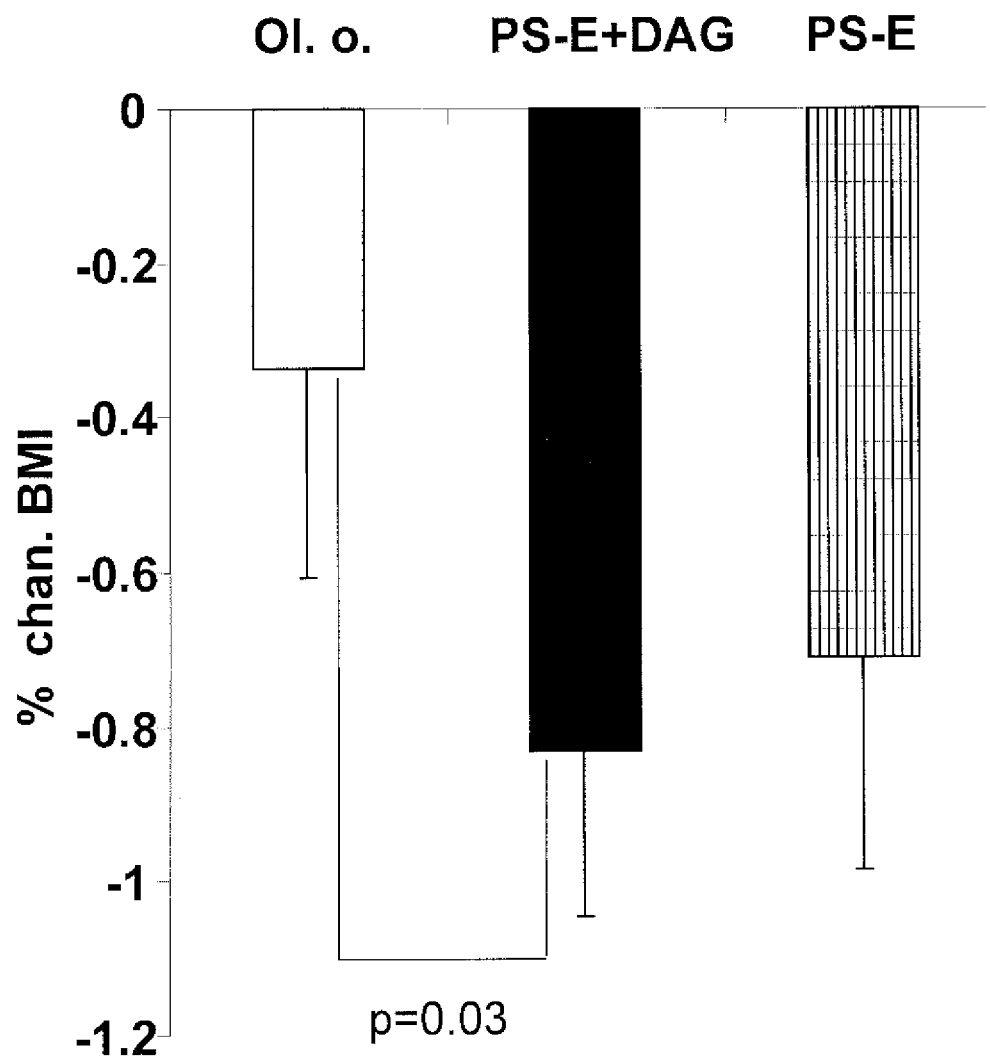

FIG. 4: PS-E+DAG-olive (Preparation B) reduces body weight

The histogram represents the percentage of change of body mass index (BMI) in females treated with olive oil, PS-E or PS-E+DAG-olive (Preparation B). Abbreviations: chan., change; ol. o., olive oil.

DETAILED DESCRIPTION OF THE INVENTION

Dietary phytosterols inhibit the absorption of dietary and biliary cholesterol, and long-term daily consumption of phytosterols induces depletion in plasma cholesterol and LDL-cholesterol concentrations. These reductions are related to a few factors, including: the dose of phytosterols consumed, the esterification of the phytosterol, the matrix the phytosterols are solubilized in, the background diet, as well as genetic factors. The main undesirable effect of administering phytosterols is that they can interfere with the absorption of many other fat-soluble dietary ingredients, such as vitamins (especially carotenoids), as well as fat-soluble drugs. Moreover, the matrix in which the phytosterols are solubilized in can clearly affect the efficacy of phytosterols in lowering LDL cholesterol. It is hypothesized that during the absorption processes in the intestine, phytosterols could displace not only cholesterol but also other lipophilic molecules and replace them in incorporation into mixed micelles. The partition into the mixed micellar phase could be influenced by the esterification and by other ingredients of the vehicle in which the phytosterols are consumed.

Scientists at Nestle's Research Centre have reported that plant sterols, added to foods to reduce cholesterol absorption, can also diminish the ability of the body to absorb beta-carotene and vitamin E [Richelle (2004) id ibid.]. This undesirable side effect is greater with the consumption of sterol esters than with free sterols. However, esterification of phytosterol is necessary for increasing the phytosterols solubility, which is crucial for the incorporation of phytosterol into micelles and inhibition of cholesterol absorption.

The present inventors have demonstrated that a combination of phytosterol and/or phytostanol ester(s) (PS-E) and DAG, mainly 1,3-diacylglycerol(s), specifically such combination in which the PS-E and DAG fatty acid moieties are mainly oleic or long chain polyunsaturated fatty acids (LC-PUFA, such as DHA and EPA) residues, as for example residues derived from olive oil, respectively fish oil, provided in the diet, conferred a beneficial health effect as part of a method of treatment for hypercholesterolemia, for example, without compromising the intake or serum levels of carotenoids, and specifically vitamin A, and even increased them.

By DAG is meant a mixture of 1,2-diglycerides and 1,3-diglycerides, containing mainly 1,3-diglycerides (about 80%).

As will be shown in the following Examples, the sterol-esters and DAG composition described herein does not adversely affect the intake of tocopherols or carotenoids upon its consumption. On the contrary, it maintains it in a steady-state level.

When referring to tocopherol, it is to be understood as including alpha- and beta-tocopherols, as well as vitamin E and other nutritionally or health beneficial derivatives. Similarly, when referring to carotenoids, it is to be understood as including alpha- and beta-carotene, lycopene, lutein, vitamin A and other nutritionally or health beneficial derivatives. Other nutritionally or health beneficial substances such as vitamin D are also contemplated within the scope of this invention.

The inventors had previously shown that a composition comprising a combination of DAG, mainly 1,3-diacylglycerol, and PS-E dissolved in canola, olive or fish oil has the property of reducing blood levels of cholesterol and triglycerides as well as lowering the oxidation levels of macrophages, serum and serum LDL in experimental animals [WO 2004/069150]. Moreover, this composition also inhibited the formation of foam cells [WO 2004/069150].

In the present study, conducted in humans, a substantial decrease in total cholesterol concentrations was observed following the fish oil treatment (LC-PUFA), while control diet consumption induced a significant though smaller hypocholesterolemic effect (Table 2). Thus, treatment with PS-E+DAG-fish (Preparation A) resulted in reduction of total cholesterol concentration, compared to diets containing no supplemented plant sterols, as well as to the omega-3 containing treatment.

PS-E+DAG-fish (Preparation A) has further proven to have potent hypocholesterolemic and hypotriglyceridemic effects, and to be suited for treatment of dyslipidemic individuals, shown to be susceptible to metabolic syndrome and diabetes.

However, due to their mechanism of action, plant sterols ester-enriched products can affect absorption of fat-soluble vitamins. Lower serum α-tocopherol concentrations following phytostanol consumption is not an unexpected finding since most tocopherol is carried in LDL particles, which are shown in numerous studies to decrease upon plant sterol consumption. Similarly, levels of several carotenoids, but especially alpha- and beta-carotene are also susceptible to change following plant sterol esters consumption, in a similar manner.

Surprisingly, the present study shows that the PS-E–DAG compositions developed by the inventors, and particularly those derived from olive oil and from fish oil, can guard and even increase the levels of circulating vitamins.

Figure 1:
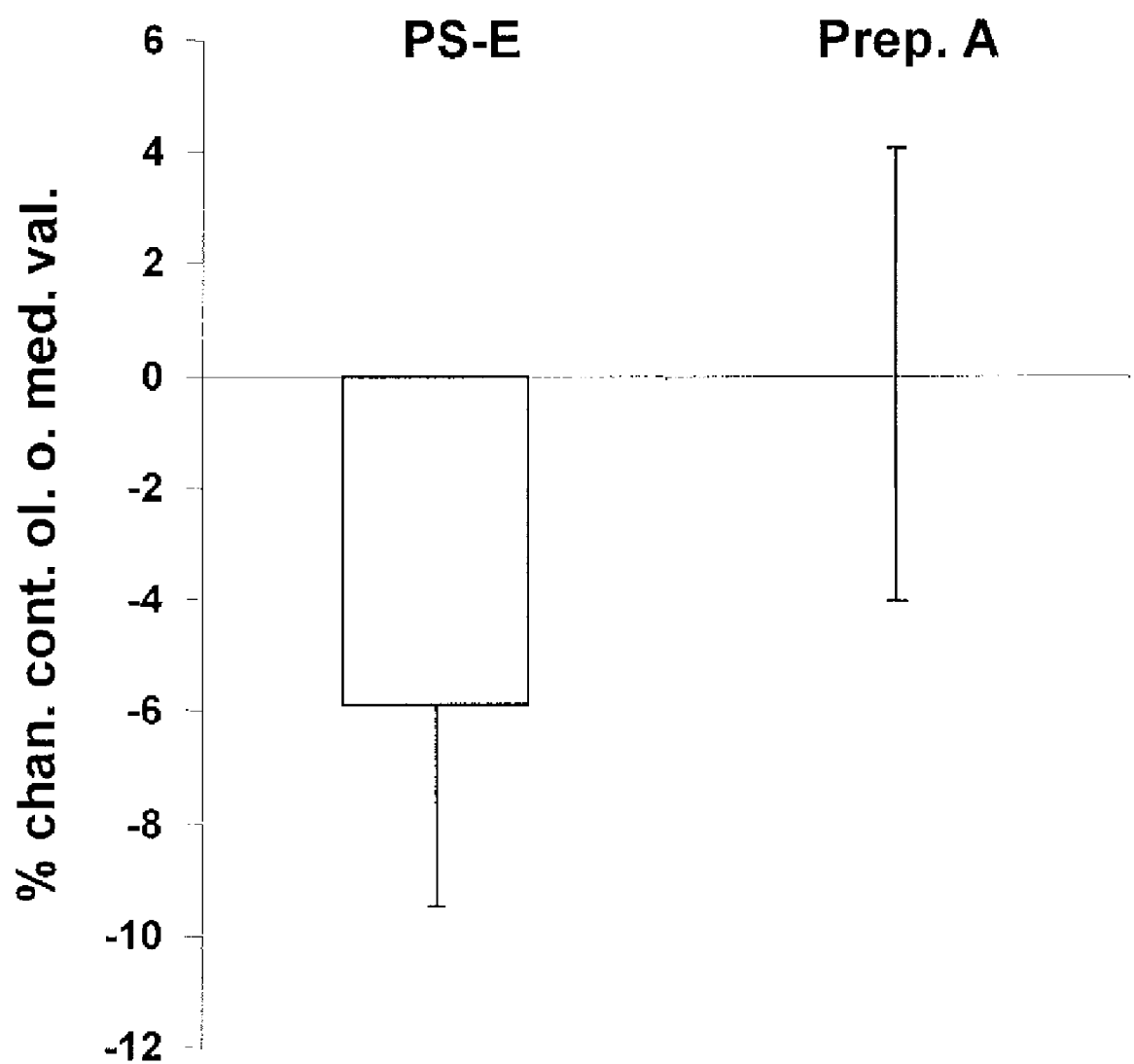
FIG. 1: Availability of plasma fat-soluble vitamins

As demonstrated in Table 4 and FIG. 1, treatment with PS-E+DAG-fish (Preparation A) resulted in an increase in the levels of vitamin A (retinol) absorption, in comparison with PS-E (P-value=0.05). Pair-wise comparison to PS-E blood levels of retinol suggested 5.1% higher concentration in subjects treated with PS-E+DAG-fish (Preparation A). FIG. 1 presents these significant differences as a percent of change from control diet median levels. These results indicate that plant sterols esters of fish oil in a DAG-containing matrix have a greater effect on Vitamin A bioavailability than PS-E with equivalent dose of phytosterols.

A similar effect was observed with β-carotene, as shown in Example 4 and FIGS. 2A, 2B and 3. When serum levels of β-carotene in volunteers treated with olive oil-based diet, PS-E and Preparation B treatments were compared (FIG. 2A), the consumption of PS-E alone resulted in a pronounced tendency (P=0.06) towards a reduction in the percentage of change of β-carotene levels, in comparison to control olive oil-based diet, whereas treatment with Preparation B (PSE+DAG-olive) of the invention resulted in comparable levels, i.e. no adverse effect on bioavailability of β-carotene. Moreover, the effect of consumption of PS-E alone on the percentage of change in β-carotene concentrations over feeding period was significantly different from that observed with Preparation B (P=0.04). Interestingly, the β-carotene levels following supplementation with Preparation A as well as fish oil (FO) did not differ from the β-carotene levels following olive oil-based diet (FIG. 2B), as opposed the aforementioned marked trend detected for PS-E treatment.

FIG. 3 depicts baseline and endpoints levels of PS-E, Preparation B, and Preparation A treated volunteers. Significant differences were observed between the changes in β-carotene concentrations following consumption of these dietary treatments (P=0.0169). Without being bound by theory, it appears that the nature of the fatty acid esterified to the plant sterol had a highly significant impact on β-carotene bioavailability. Importantly, consumption of PS-E alone resulted in a statistically significant different effect on the change in β-carotene levels (P=0.0139) when compared to consumption of Preparation A. These results demonstrate a superior effect of Preparation A, and to some extent of Preparation B, on circulating beta-carotene levels in comparison with PSE.

Thus, it is of major importance that PS-E+DAG-fish (Preparation A) and PS-E+DAG-olive (Preparation B), besides their hypocholesterolemic effect, also maintained the blood levels of fat-soluble vitamins. This makes the composition described herein an important improvement in the field of phytosterol-based therapies. As mentioned before, phytosterols have been widely used for lowering circulating cholesterol. However, due to their capacity to "absorb" circulating lipid molecules, phytosterols can also affect the levels of other circulating lipid or lipophilic molecules, and thus become harmful to the body. Nonetheless, the compositions presented herein not only did not have this adverse effect, but exhibited an effect of increasing serum levels of these vitamins.

Therefore the compositions provided by the present invention provide an advantage over similar compositions presently available in the market, in that they promote protection to the levels of circulating vitamins. Similarly, it may be expected that also the levels of other lipophilic molecules, such as lipophilic drugs or other pharmaceutically active ingredients, including nutrients, shall be guarded upon consumption of the PS-E–DAG compositions provided herein.

The amount of the therapeutic or pharmaceutical composition of the invention which is effective in the treatment of a particular disease, condition or disorder will depend on the nature of the disease, condition or disorder and can be determined by standard clinical techniques. In addition, in vitro assays as well as in vivo experiments may optionally be employed to help identify optimal dosage ranges. Effective doses may be extrapolated from dose-response curves derived from in vitro or animal model test systems.

The therapeutically effective amount for purposes herein is that determined by such considerations as are known in the art. The amount must be sufficient, e.g., to enable the lowering cholesterol effect of phytosterols, while not adversely affecting the bioavailability of other lipophilic molecules, such as vitamins, or pharmaceutically active ingredients such as statins, and other lipophilic drugs or dietary ingredients.

The various methods of treatment as well as the method of improving weight management provided in the present invention involve administering a therapeutically effective amount of a mixture of PS-E and DAG dissolved or dispersed in an edible oil or fat, or a composition or food article comprising thereof, as described herein. The preferred method of administration of the mixture, composition or food article, as might be the case, is oral. The food article may be a solid food article, a beverage, a spread or a paste.

In other words, the compositions or mixtures described herein are primarily for the treatment of conditions that require phytosterol therapy, and in that context maintain the bioavailability of lipophilic circulating molecules, like vitamins, lipophilic drugs, lipophilic nutrients, etc., in contrast to known phytosterol preparations. Alternatively, said compositions are also to be used in parallel or in combination with the treatment of other conditions, which require the use of lipophilic drugs, such as for example certain analgesics, anesthetics, immune suppressors, HIV-protease inhibitors, anti-malaria drugs, psychotropic agents, amongst others.

The compositions described herein have also demonstrated properties with regards to treating obesity. Obesity is an escalating problem worldwide and a major risk factor for atherosclerosis, hypertension and type 2 diabetes. As shown in Example 4, the average BMI levels demonstrated a tendency to reduction upon treatment with the PS-E+DAG-olive (Preparation B) composition, particularly in females. As shown in FIG. 4, the biggest and the most significant effect on reducing BMI levels, as compared with control, was obtained as a result of PS-E+DAG-olive (Preparation B) supplementation.

To date, no comparable results of BMI reduction following phytosterols interventional study were reported, including a recent publication in which similarly restricted diet was provided to diabetic and non-diabetic subjects [Lau et al. (2005) Am J. Clin. Nutr. 81:1351-1358]. Although the connection between obesity, dyslipidemia and diabetes is well documented, there has been no report of a drug, or dietary supplement, that provides the reduction of blood lipid levels, BMI, while maintaining the fat-soluble vitamin levels.

Thus it is a purpose of the invention to provide a method of treatment to a variety of disorders requiring addressing hypercholesterolemic conditions or preventive/maintenance treatment for populations for which the development of a hypercholesterolemic conditions or its escalation may make said population prone to develop a more severe health condition, such as CVD, CHD, atherosclerosis or a metabolic syndrome, such as diabetes type 2 or obesity. In addition, the following conditions may also be treated with the composition described herein: cancer, benign prostatic hypertrophy, ulcer, prostatitis, pulmonary tuberculosis, human immunodeficiency virus (HIV), stress-induced immune suppression, rheumatoid arthritis, and allergic rhinitis/sinusitis. In this context, these methods of the invention are particularly valuable for those patients that exhibit reduction in levels of lipophilic vitamins as a result from conventional phytosterol therapy, but are of course beneficiary also to other patients.

Hyperlipidemia is common after transplantation and is usually characterized by increased total cholesterol. The etiology of post-transplantation dyslipidemia is multifactorial but is, in part, related to immunosuppressive drugs given in combination that commonly leads, as side effect, to increased circulating cholesterol levels. Other patients who receive immunosuppressive drugs (such as autoimmune patients) suffer as well from dyslipidemia. There is a clear association between cardiovascular disease and post-transplantation hyperlipidemia. Control of hyperlipidemia is an important factor that affects the graft and patient wellbeing and survival, thus frequently the use of statins or combination of statins and phytosterols is necessary for controlling the cholesterol levels. The use of conventional phytosterol preparations may inhibit the absorption of vitamins which are particularly needed for this special population.

Transplant patients are also at a higher risk of 25(OH)D deficiency because of their need to protect themselves from sun exposure. Thus, treatment with vitamin D is recommended to correct their vitamin D deficiency, which may help protect these patients from serious vitamin D deficiency-related health problems that include an increased risk for bone loss and internal malignancies. Using the invention formulation of phytosterols can eliminate or at least decrease the negative vitamin absorption effect of phytosterols.

Vitamin A is needed for proper immune system functioning. Since grafted patients receive immunosuppressive drugs in order to protect the graft from rejection, it is extremely important to protect the patients from further reduction in the activity of the immune system. Using the invention formulation of phytosterols can increase the vitamin A absorption in comparison to conventional phytosterol preparations, resulting in a more potent immune system.

Other groups which are on need of phytosterol therapy and suffer from immune suppression may also benefit from the unique formulation of the invention. These groups include cancer patients, HIV patients, stress-induced immune suppression patients, immune suppression patients receiving any treatment resulting in suppression of the immune system, autoimmune patients, radiation-treated patients, chemotherapy-treated patients and patients suffering from allergic rhinitis/sinusitis.

Vitamin D inadequacy is very common among the elderly, and is implicated in the development of osteopenia and osteoporosis. Vitamin D inadequacy has also been implicated as a contributing factor to hyperparathyroidism muscle weakness and falls [Gaugris et al. (1998) Q. J. Med. 98:667-676]. Since the elder population is very susceptible to dyslipidemia, they are frequently in need of phytosterol therapy. Thus, the present invention can answer their need for phytosterol therapy, while not further disturbing their vitamin levels, or, in comparison with conventional phytosterol formulation, increasing their vitamin levels.

Children and adolescents suffering from dyslipidemia such as type I or type II diabetes mellitus, and familial hypercholesterolemia [De Jongh et al. (2003) J Itherit Metab Dis. 26(4):343-51] have been reported to be treated with phytosterols in order to control their cholesterol levels. Since this population is more susceptible to vitamins deficiency it is beneficial to treat it with the present invention.

Phytosterols are added to different food articles such as spreads, and these products are consumed by the whole family, including children and adolescents. Replacing the conventional phytosterols with the phytosterols of the invention, can eliminate the possibility of reducing the vitamin levels in these sensitive populations. This advantage is of great importance since recently it has been reported that vitamin D deficiency has a high prevalence in otherwise completely healthy adolescents [Gordon et al (2004) Arch Pediatr Adolesc Med. 158(6):531-7]. Children with vitamin D deficiency are at greater risk for stunted growth and weakened bones that are prone to fractures and osteoporosis later in life. As a matter of fact, severe and prolonged vitamin D deficiency is the cause of rickets. The composition of the invention is beneficiary not only for treating or preventing vitamin D deficiency, but also of other vitamins and essential nutrients such as vitamin A, tocopherol and β-carotene.

Thus, generally, the methods of the invention are intended for the above described patients, who may suffer from impaired vitamin absorption, patients prone to vitamin malabsorption due to medical treatment in which they are in need, special populations as the elderly population, and children, who are more susceptible to vitamin malabsorption.

Said methods of treatment include providing phytosterols, preferably phytosterol esters, in combination with diglycerides, and optionally triglycerides, to achieve reduction of blood cholesterol levels while maintaining and even increasing normal intake levels of other lipophilic active ingredients and/or nutrients. Said active ingredients may be pharmaceutical ingredients, such as statins, used to lower cholesterol levels by inhibition of the biosynthetic pathway of their production. Treatments using statins and phytosterols have been shown to have an additive beneficial effect. Additionally, said ingredients may be anti-oxidants, preferably natural carotenoids anti-oxidants, such as lutein, beta-carotene, and lycopene. The use of such anti-oxidants is beneficial in this context since most target populations for the treatment described herein suffer or are prone to suffer from oxidative stress, which may worsen their cardiovascular or metabolic syndrome condition. Further ingredients may also include Omega-3 LC-PUFA, especially DHA and EPA.

The results described in Example 4 show that circulating levels of phytosterols can be affected by modification in the diet. Moreover, consumption of the PS-E+DAG-fish composition of the invention increased the bioavailability of phytosterols and stanols, such as beta-sitosterol, compared to PS-E diet. Thus, the composition described herein may definitely enhance the efficacy of phytosterols as anti-cancer agents, as well as their other health benefits.

Additionally, a number of conditions may arise from decreased levels of fat-soluble vitamins, and thus subjects suffering from or prone to develop said conditions are very good candidates for therapeutic and/or prophylactic treatment with the composition described herein, which sustains the levels of circulating vitamins. Among said conditions are stroke, diabetes, breast cancer, immune deficiency, immune suppression, osteoporosis, osteopenia, photo-aging, skin tumor, photosensitivity reaction, cataractogenesis and cataracts, retinal photodeterioration, erythrocyte photochemolysis, photoerythema, photo-carcinogenesis, Crohn's disease, short bowel syndrome, Alzheimer's disease, dementia, infantile nonalcoholic steatohepatitis, multiple sclerosis.

In particular, lipophilic active ingredients such as dietary lipophilic vitamins, and other dietary lipophilic nutrients whose normal intake is crucial for maintaining a good general health condition, are important targets of the method of treatment described herein. In a preferred embodiment said dietary lipophilic vitamins are carotenoid or tocopherol based and include β-carotene, vitamin A, vitamin E, their provitamins and their isomers and derivatives, as well as vitamin D. In some cases said carotenoid and/or tocopherol vitamins are considered as anti-oxidants.

In general, the absorption of a variety of other lipophilic molecules such as pharmaceutical ingredients and phyto-ingredients that partition into the intestinal oil/micelle phase is compromised by the phytosterols poor solubility. Thus, the method of treatment of the invention provides the means to treat hypercholesterolemic conditions or pro-hypercholesterolemic conditions, or other conditions, without inhibiting the intake or bioavailability of other active ingredients or dietary nutrients whether these are needed to treat the same or related aspects of the condition (CVD, CHD, metabolic syndromes) or other health conditions or disorders which the intake of the active ingredients required for their treatment may be compromised by the parallel treatment with phytosterols or their esters.

Thus, a yet further aspect of the present invention is to provide a method of treating and/or preventing conditions related to metabolically-induced overweight, said method consisting of administering a therapeutically effective amount of the dietary nutrient or food supplement, or the composition of the invention, as previously described. Said conditions are any one of obesity, diabetes, hypercholesterolemia and metabolic syndrome.

Thus, according to the invention, as part of the method of treatment, said combination of phytosterol esters, while addressing hypercholesterolemia and maintaining adequate intake levels of other lipophilic active ingredients or dietary nutrients, provides also weight control and even weight reduction. As discussed above, weight control and/or reduction are important parts of the treatment and/or prevention of the health conditions addressed by this method of treatment.

The compositions of the invention provide a platform for the delivery of phytosterols to patients in various conditions requiring phytosterol treatment, or in which such treatment may be beneficial, where the phytosterols are more bioavailable than phytosterols in conventional preparations are, and where the delivery does not adversely affect, and even increases the bioavailability of the various lipophilic agents, such as all those listed above.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Methods

Human Clinical Study Design

This study was designed as a randomized, single-blind, cross-over clinical intervention trial. This experiment involved testing the effects of dietary matrices containing specific fatty acid and/or plant sterol mixtures included in normal diets, compared to non-supplemented diets, on vitamins absorption and on weight gain, in moderately overweight subjects with elevated serum lipid levels for whom dietary modification is the primary and at times only therapeutic recommendation.

Patients

Twenty-four (24) volunteers (11 male, 13 female, age 30-65 yr) with LDL-cholesterol concentrations>130 mg/dL were recruited for this study. Body mass indices (BMI) of subjects ranged from 23-32 kg/m$^2$, except for three subjects in which BMI was between 21.4 and 23 kg/m$^2$. Twenty-one volunteers completed the study (11 male, 10 female).

Diets

All volunteers underwent a feeding trial according to a semi-randomized Latin square cross-over design containing five dietary phases, each four week in duration. The control diet was provided first, then the other phases randomized. Each feeding period was separated by a 4-week washout interval, during which volunteers consumed their typical diets without restriction. The composition of the diets was similar with respect to the food and nutrient content. The basic diet contained 30% of energy as fat (see control diet), 80 mg cholesterol/1000 kcal, 12 g fiber/1000 kcal, 15% energy as protein and 55% as carbohydrates. The variable component was the treatment oil.

Diets were designated as:

Control group: baseline plant sterol level of about 200 mg/day, where the dietary fat was comprised at 70% energy as oleic acid-enriched vegetable oil.

LC-PUFA group: 7.6 g/day of fish oil providing the same amount of EPA and DHA as the plant sterol-fish oil ester diet.

PS-E+DAG-fish (Preparation A) (Omega-3-esters mixture) group: 1.7 g/day soy sterols esterified to fish oil fatty acids (including EPA and DHA), contained in a diglyceride and triglyceride containing fish oil (commercial fish oil, manufactured by Pronova, Lysaker, Norway) (total amount=9 g/d).

PS-E: 1.7 g/d soy sterol esterified to polyunsaturated fatty acids like linolic acid (LA) and OA, which resembles the commercially available phytosterol esters product.

PS-E+DAG-olive (Preparation B) (PS-E+DAG) group: 1.7 g/day soy sterols esterified to olive oil fatty acids (predominantly oleic acid), contained in a diglyceride (DAG) and triglyceride containing olive oil (commercial extra virgin olive oil, manufactured by Meshek Eger, Yokeneam HaMoshava, Israel) (total amount=9 g/d).

TABLE 1

Composition of Preparation A and Preparation B

| Oil components % (w/w) | PS-E + DAG in Fish oil (Preparation A) | PS-E + DAG in Olive oil (Enzymotec FG S7/1.75) (Preparation B) |
|---|---|---|
| Phytosterol esters | 22.12 | 28.5 |
| Monoglycerides | 4.72 | 1.48 |
| Diglycerides | 20.02 | 14.62 |
| Triglycerides | 40.3 | 48.9 |
| Free sterols | 5.2 | 1.5 |
| FFA | 5 | 5 |
| Glycerol | 2.6 | N.D. |
| Brassicasterol* | 0.82 | 0.46 |
| Campasterol* | 4.93 | 4.58 |
| Stigmasterol* | 3.25 | 3.86 |
| Betasitosterol* | 8.1 | 8.41 |

*levels of the different sterols, which can be either esterified or non-esterified All meals were equicaloric and breakfast was consumed each day under supervision. The treatment oil was given within the breakfasts consumed every day at the clinic under supervision. Volunteers were instructed to eat and drink only materials given to them by the Clinical Nutrition Research Unit (McGill University, Montreal, Canada), except for water. Study volunteers were encouraged to maintain their usual level of physical activity. Energy requirements were estimated using the Mifflin equation and multiplied by an activity factor of 1.7. Energy intakes were adjusted over the initial 2-week period to maintain constant body weight and kept constant for the remaining 4 weeks and the other treatment phases.

Blood Analyses

On days 1, 2, 28 and 29, blood samples were obtained in the fasting state. Plasma was immediately separated and stored at −80° C. until analysis. Total cholesterol, phytosterol, as well as triglycerides levels, were measured in samples taken on days 1, 2, 28 and 29 of each phase. Levels of plasma total cholesterol and triglyceride were determined by automated methods in duplicate on an Abbott Spectrum CCX Analyzer (Abbott, Dallas, Tex.) utilizing enzymatic reagents (Abbott A-GENT). Plasma phytosterol concentrations were determined by GLC (HP5890 series II: Hewlett-Packard). Vitamin E ($\alpha$-tocopherol), beta-carotene and Vitamin A (retinol) levels were measured in samples from days 1, 2, 28, and 29, and quantified through HPLC. Plasma leptin levels were determined at the end of each phase through radioimmunoassay.

Anthropometric Measurements:

The following determinations were performed in triplicates at the beginning (days 1, 2, and 3) and termination (days 27, 28, and 29) of each of the five dietary phases. Weight was measured daily before breakfast in light clothing without shoes. Height was measured as the distance from the top of the head to the bottom of the feet (no shoes) using a fixed stadiometer. BMI was calculated as the weight (kg) divided by the square of the height (m).

Example 1

Hypocholesterolemic Effect of PS-E+DAG-Fish (Preparation A)

Hypercholesterolemic overweight volunteers were fed for four weeks with control diet, LC-PUFA oil, PS-E+DAG-fish (Preparation A) or PS-E followed by four weeks of washout and counter supplementation. Total cholesterol levels were tested at the beginning and at the termination of each phase as described in methods. The results are shown in Table 2. Values represent mean±S.E.M of the total cholesterol levels in 21 patients at the indicated time points as well as percent of change. Statistical significance between the different treatments as found by one-way ANOVA followed by Tukey's post hoc test between the percent of change values was P-value<0.1. Means with different superscript letter are significantly different, P<0.05.

As shown in Table 2, both the baseline and the endpoint of the total cholesterol concentrations were comparable in all subjects through the different diet phases consumption (P-value=0.99 and 0.61, respectively). However, all these treatments induced a significant reduction in the percentage of total cholesterol concentrations, although to different degree (P-value=0.057). Post Hoc evaluations suggest PS-E+DAG-fish (Preparation A) to demonstrate the most pronounced positive effect in this parameter, i.e. decreased the total cholesterol levels.

TABLE 2

Total cholesterol concentrations

| Parameter (Total cholesterol in mmol/L) | Baseline values | Endpoint values | % of change |
|---|---|---|---|
| Control | 6.23 ± 0.27 | 5.90 ± 0.22 | −4.4$^a$ ± 2.1 |
| LC-PUFA | 6.23 ± 0.22 | 5.69 ± 0.23 | −8.5$^{ab}$ ± 2.3 |
| Preparation A | 6.28 ± 0.24 | 5.48 ± 0.23 | −12.5$^b$ ± 2.2 |
| PS esters | 6.25 ± 0.24 | 5.61 ± 0.21 | −9.9$^{ab}$ ± 1.8 |

Example 2

Hypotriglyceridemia Effect of PS-E+DAG-Fish (Preparation A)

Hypercholesterolemic overweight volunteers were fed for four weeks with control diet, LC-PUFA oil, PS-E+DAG-fish (Preparation A) or PS-E followed by four weeks of washout and counter supplementation. Triglycerides levels were tested at the beginning and at the termination of each phase, under fasting conditions, as described in methods. The results are shown in Table 3. Values represent mean±SEM of triglycerides levels in 21 patients at the indicated time points as well as percent of change. Statistical significance between the different treatments as found by one-way ANOVA followed by Tukey's post hoc test between the endpoint values was P-value<0.01 and between the percent of change was P-value<0.001. Means with different superscript letter are significantly different, P<0.05.

As previously shown for the plasma cholesterol containing component of these volunteers, the baseline values were virtually similar (P-values=0.33). The end result of administrating these treatments was shown to be beneficial in reducing triglycerides levels in these hypercholesterolemic subjects. However, there was an unambiguous difference between the efficacy of omega-3 containing treatments to the other fatty acids diets (P-value=0.0036). Un-reacted fish oil decreased plasma fasting triglycerides by 37.1% (P-value-0.007) while the comparable effect of the omega-3 esters mixture of the invention (PS-E+DAG-fish (Preparation A)) was 42.9% decrease (P-Value=0.00002), yet there was only a mild tendency that suggests a difference between the effects of these supplementations (Student's t-test Paired analysis the P-value-0.112). Comparing the effects of these supplements on fasting triglycerides levels to the rather mild effect of the control diet (−5.3%; P-Value=0.04) and PS-E (−8.7%; P-value=0.04) provides a statistically significant difference between the consumption of fish oil to vegetable oil (see Table 3).

TABLE 3

Plasma fasting triglycerides concentrations

| Parameter (Total cholesterol (mmol/L)) | Baseline values | Endpoint values | % of change |
|---|---|---|---|
| Control | 2.16 ± 0.36 | 1.86$^a$ ± 0.27 | −5.3$^a$ ± 5.4 |
| LC-PUFA | 2.01 ± 0.33 | 1.10$^b$ ± 0.13 | −37.1$^b$ ± 4.4 |
| Preparation A | 1.86 ± 0.25 | 0.99$^b$ ± 0.12 | −42.9$^b$ ± 3.9 |
| PS esters | 1.84 ± 0.23 | 1.62$^a$ ± 0.19 | −8.9$^a$ ± 5.9 |

Example 3

Plasma Fat-Soluble Vitamins Levels

Vitamin A Level

Hypercholesterolemic overweight volunteers were fed for four weeks with control diet, LC-PUFA oil, PS-E+DAG-fish (Preparation A) or PS-E followed by four weeks of washout and counter supplementation. Vitamins levels were tested at the termination of each phase, as described in methods. The results are shown in FIG. 1 and Table 4. Values represent mean±SEM of vitamin A levels obtained from 21 patients in Table 4 and as % of change from control diet median in FIG. 1. Statistical significance between the different treatments as found by Student's t-test Paired analysis was p-value<0.05.

TABLE 4

| Treatment | Vitamin A in plasma [μg/dL] |
|---|---|
| Olive oil | 68.2 ± 2.5 |
| PS-E | 65.0 ± 2.3 |
| Preparation A | 69.1 ± 2.3$^a$ |

$^a$Significant increase in comparison with PS-E (pvalue = 0.05)

Supplementation with plant sterols diet, i.e. PS-E, resulted in reduction (−5%) of the bioavailability of vitamin A (retinol) compared to the control olive oil (65.0±2.3 μg/dL, and 68.2±2.5 μg/dL, respectively). However, supplementation with Preparation A (a combination of plant sterols and diglycerides in fish oil) was shown to be comparable to control diet levels (P-value=0.41) and demonstrated a small, yet significant increase in vitamin A plasma concentrations compared to consumption of the PS-E diet (69.1±2.3 μg/dL and 65.0=2.5 μg/dL, respectively; P-value=0.05). Consistent with this trend, the paired change of the hypercholesterolemic subject vitamin A concentration between the endpoint levels following PS-E and PS-E+DAG-fish (Preparation A) diets, suggested that the latter diet consumption resulted in 5.1% higher plasma vitamin A levels. Similar observations were obtained comparing vitamin A levels to control diet median value (see FIG. 1).

Beta-Carotene

The experiment was repeated for β-carotene plasma levels in a group of 5-7 volunteers. Beta-carotene concentrations were tested at the beginning and end of each treatment phase. Baselines and endpoints concentrations of β-carotene were compared between volunteers receiving (A) olive oil (OO)-based diet (control), PS-E and Preparation B treatment; and (B) olive oil (OO)-based diet, fish oil (LC-PUFA (fish oil) treatment, PS-E and Preparation A. The results are shown in FIGS. 2A and 2B. The dietary treatments did not affect the percentage of change of plasma β-carotene concentrations. Nonetheless, when olive oil-based diet, PS-E and Preparation B treatments were compared (FIG. 2A), the consumption of PS-E alone resulted in a pronounced tendency (P=0.06) towards a reduction in the percentage of change of β-carotene levels (−1%±11%), in comparison to control olive oil-based diet (OO) (38%±15%)) whereas the Preparation B treatment resulted in comparable levels (23%±14%), i.e. no adverse effect on bioavailability of β-carotene. Moreover, the effect of consumption of PS-E alone on the change in β-carotene concentrations over feeding period was significantly different from that observed with Preparation B (P=0.04). Interestingly, the β-carotene levels following supplementation with Preparation A (18%±10%) as well as fish oil (FO) (24%±18%) (FIG. 2B) did not differ from the β-carotene levels following olive oil-based diet, as opposed the aforementioned marked trend detected for PS-E treatment.

Next, the effect of PS matrices, esterified with fatty acid originating from different sources on β-carotene concentrations was tested in all study participants (n=21), by comparing the baseline and endpoints levels in PS-E, Preparation B, and Preparation A receiving volunteers. Significant differences were observed between the changes in β-carotene concentrations following consumption of these dietary treatments (P=0.0169). It appears that the nature of the fatty acid esterified to the plant sterol had a highly significant impact on β-carotene bioavailability (FIG. 3). Importantly, consumption of PS-E alone resulted in a statistically significant different effect on the change in β-carotene levels (P=0.0139) when compared to consumption of Preparation A. Preparation B supplementation effect on the β-carotene levels did not differ from that of preparation A.

Example 4

Effect of PS-E+DAG-Fish (Preparation A) on Plasma Plant Sterols Concentrations

Hypercholesterolemic overweight volunteers were fed for four weeks with control diet, LC-PUFA oil, PS-E+DAG-fish (Preparation A) or PS-E followed by four weeks of washout and counter supplementation. Phytosterols levels were tested at the beginning and at the termination of each phase, as described in methods. The results are shown in Table 5. Values represent mean±SEM of beta-sitosterol levels in 21 patients at the indicated time points as well as percent of change. Statistical significance between the different treatments as found by one-way ANOVA followed by Tukey's post hoc test between the endpoint values was P-value<0.05 and between the percent of change was P-value<0.001. Means with different superscript letter are significantly different, P<0.05.

There were no differences between treatments groups at baseline (P-value=0.44). However, the post-treatment values demonstrated significant differences between the indicated diets (P-value=0.03). These differences were more striking in the percent of change, as shown in Table 5 (P-value=0.0003). Both plant sterol containing diets demonstrated a marked increase in this parameter, nevertheless as evaluated by Student's t-test Paired analysis there was a distinct tendency between the effects of these supplementations (the P-Value=0.058). Comparable trend was obtained when the beta-sitosterol values were standardized to the cholesterol levels at the end of these dietary phases.

TABLE 5

Beta-sitosterol concentrations

| Parameter (Beta-sitosterol in mmol/L) | Baseline values | Endpoint values | % of change |
|---|---|---|---|
| Control | 6.01 ± 0.60 | 5.48$^c$ ± 0.61 | −8.4$^c$ ± 3.6 |
| LC-PUFA | 7.38 ± 0.79 | 6.93$^b$ ± 0.79 | −6.0$^b$ ± 3.8 |
| Preparation A | 6.79 ± 0.69 | 8.31$^a$ ± 0.89 | 26.8$^a$ ± 9.2 |
| PS esters | 6.94 ± 0.91 | 7.62$^{ab}$ ± 0.94 | 13.4$^{ab}$ ± 6.6 |

The human body does not synthesize phytosterols endogenously. Circulating phytosterols are derived exclusively through intestinal absorption. Serum phytosterol levels in humans range from 6 to 41 μmol/L. Thus, the fact that the absolute change in beta-sitosterol concentration was greater in the preparation A dietary intervention group than in the PS-E group clearly demonstrates that sterol levels were affected according to the diet consumed. These results show that circulating levels of phytosterols can be affected by dietary modification. Moreover, consumption of the sterol-esters and DAG composition of the invention may increase the bioavailability of phytosterols and stanols, such as beta-sitosterol, compared to PS-E diet, hence enhancing their efficacy as anti-cancer agents as well as other health benefits.

Example 5

Body Weight Gain

Hypercholesterolemic mildly overweight volunteers were fed for four weeks with control diet, LC-PUFA oil, PS-E+DAG-fish (Preparation A), PS-E or PS-E+DAG-olive (Preparation B) followed by four weeks of washout and counter supplementation. Bodyweight levels were tested at the beginning and at the termination of each phase, as described in methods and BMI values were subsequently calculated. The % of change in BMI results for females are shown in FIG. 4. Values represent mean±S.E.M of % of change in BMI in 10 female patients. Statistical significance between the indicated treatments as found by Student's t-test Paired analysis was P-value<0.05.

As indicated in methods, 21 subjects completed all five diet periods. There were no differences in the energy intake among the five dietary groups. Weight was measured using a standard scale and BMI was calculated as the weight (kg) divided by the square of the height (m²). Initial and end-point BMI levels were calculated as the average of BMI measurements taken on the beginning (days 1, 2, and 3) and end (days 27, 28, and 29) of each of the five dietary phases.

In the present study there was a slight however distinct decrease from baseline to endpoint BMI values in all five diet-periods (control 26.00±0.62 to 25.81±0.59, P-value=0.01; LC-PUFA 26.31±0.69 to 26.17±0.65, P-value=0.10; PS-E+DAG-fish (Preparation A) 26.10±0.69 to 26.02±0.68, P-value=0.10; PS-E 26.27±0.64 to 26.14±0.63, P-value=0.01; Preparation B 26.18±0.63 to 26.00±0.62, P-value=0.001).

Further evaluation of the change between the baseline to the endpoint levels of the BMI values in males and females, suggest that these vegetable oil based plant sterol treatments were more efficacious in reducing females BMI levels than these treatments comparable effect in mildly overweight males; average change from baseline to endpoint in control, PS-E and PS-E+DAG-olive (Preparation B) females was −0.09±0.02, −0.22±0.02 and −0.18±0.02, respectively, and in males −0.29±0.03, −0.14±0.02 and −0.09±0.02, respectively. Using a paired analysis to compare the percent change of the BMI values between these female subjects (n=10) was shown to be more prominent following supplementation with PS-E+DAG-olive (Preparation B) compared with control olive oil diet (P-value=0.03; see FIG. 4). This distinct and significant reduction in % of change of BMI levels in females, was not obtained comparing the control and PS-E supplement (P-value=0.28), indicating that the dietary matrix PS-E+DAG-olive (Preparation B) was more effective in reducing body weight than PS-E (FIG. 4). Interestingly, these discrete effects on BMI levels between males and females presented by plant sterols containing diets were further correlated with a corresponding reduction in fasting leptin levels in females, in compared with control endpoint levels (−8.6±6.3% and −6.9±7.1% for Preparation B and PS-E), while similar analyses for males resulted with a contrary effect (2.1±6.3% and 6.5±4.6% for Preparation B and PS-E).

The invention claimed is:

1. A method of increasing or maintaining bioavailability of at least one lipophilic vitamin in a patient receiving phytosterol therapy, wherein the bioavailability of said at least one lipophilic vitamin in said patient is reduced as a result of said phytosterol therapy, said method comprising administering to said patient a therapeutically-effective amount of a mixture of (1) phytosterol ester(s) and/or phytostanol ester(s) (PSE) with (2) 1,3-diglyceride(s) (DAG) dissolved or dispersed in an edible fish oil, wherein fatty acid residues of the PS-E and of the DAG correspond to fatty acid residues of fish oil.

2. The method of claim 1 wherein said patient receiving phytosterol therapy suffers from deficiencies in fat-soluble vitamins resulting from said therapy.

3. The method of claim 2, wherein said deficiencies in fat-soluble vitamins result from at least one of a metabolic disorder, malabsorption of fats, drug-vitamin direct or indirect interactions impaired vitamin absorption.

4. The method of claim 3, wherein said patient also suffers from a condition selected from the group consisting of cancer, benign prostatic hypertrophy, organ transplant, ulcer, prostatitis, cardiovascular disorder (CVD), coronary heart disease (CHD), atherosclerosis, pulmonary tuberculosis, human immunodeficiency virus (HIV), stress-induced immune suppression, rheumatoid arthritis, patients receiving any treatment resulting in immunosuppression, autoimmune patients, radiation-treated patients, chemotherapy-treated patients, and allergic rhinitis/sinusitis.

5. The method of claim 1, wherein said patient receiving phytosterol therapy is a patient that suffers from an immune deficiency including human immunodeficiency virus (HIV), stress-induced immune suppression, rheumatoid arthritis, patients receiving any treatment resulting in immunosuppression, autoimmune patients, radiation-treated patients, chemotherapy-treated patients, allergic rhinitis/sinusitis, and organ transplant patients.

6. The method of claim 5, wherein said immune deficiency, is accompanied by an increase in serum cholesterol levels.

7. The method of claim 1, wherein said patient receiving phytosterol therapy is a child suffering from a vitamin or essential nutrient deficiency, including β-carotene, vitamin A, and vitamin D deficiencies.

8. The method of claim 1, wherein said at least one lipophilic vitamin is a carotenoid.

9. The method of claim 8, wherein said at least one lipophilic vitamin is vitamin A or vitamin D.

10. The method of claim 1, wherein the fatty acid residues of the PS-E and of the DAG are docosahexaenoic (DHA) and eicosapentaenoic acid (EPA) residues.

11. The method of claim 1, wherein the phytosterol ester(s) are fatty acid ester(s) of a phytosterol selected from the group consisting of stigmasterol, sitosterol, beta-sitosterol, brassicasterol, campesterol, 5-avenasterol, and isomers and derivatives thereof and said phytostanol ester(s) are fatty acid ester(s) of a phytostanol selected from the group consisting of beta-sitostanol, campestanol, stigmastanol, and isomers and derivatives thereof.

12. The method of claim 1, wherein a weight ratio between phytosterol and/or phytostanol esters and diacylglycerol(s) and phytosterol and/or phytostanol ester(s) in said mixture is from 15:1 to 1:1.

13. The method of claim 1, wherein an amount of diacylglycerol(s) in said mixture is at least 1 wt %.

14. The method of claim 1, wherein an amount of phytosterol and/or phytostanol ester(s) in said mixture is at least 1 wt %.

15. The method of claim 1. wherein an amount of diacylglycerol(s) in said mixture is from 1 to 99 wt %.

16. The method of claim wherein said mixture consists of 15 wt % DAG of which more than 50% are 1,3-DAG(s) and 25 wt % total PS-E(s) dissolved or dispersed in fish oil.

17. A method of increasing or maintaining bioavailability of at least one lipophilic vitamin in a patient receiving phytosterol therapy, wherein the bioavailability of said at least one lipophilic vitamin in said patient is reduced as a result of said phytosterol therapy, said method comprising administering to said patient a therapeutically-effective amount of a mixture consisting of (1) phytosterol ester(s) and/or phytostanol ester(s) (PS-E) with (2) 1,3-diglyceride(s) (DAG) dissolved or dispersed in fish oil wherein tai acid residues of the PS-E and of the DAG correspond to fatty acid residues of fish oil.

18. The method of claim 17, wherein the fatty acid residues of the PS-E and of the DAG are docosahexaenoic (DHA) and eicosapentaenoic acid (EPA) residues.

19. The method of claim 1, wherein said mixture is comprised in a food article.

20. The method of claim 17, wherein said mixture is comprised in a food article.

* * * * *

UNITED STATES PATENT AND TRADEMARK OFFICE
CERTIFICATE OF CORRECTION

PATENT NO.         : 8,772,270 B2                              Page 1 of 1
APPLICATION NO.    : 11/673726
DATED              : July 8, 2014
INVENTOR(S)        : Avidor Shulman et al.

It is certified that error appears in the above-identified patent and that said Letters Patent is hereby corrected as shown below:

In the Claims

Amend Claims 1-3 as follows:

Claim 1, Column 26, line 52, after "wherein" insert --the--.

Claim 2, Column 26, line 55, after "said" insert --phytosterol--.

Claim 3, Column 26, line 60, after "interactions" insert --and--.

Amend Claims 12, 16 and 17 as follows:

Claim 12, Column 28, lines 3, delete "and phytosterol and/or phytostanel ester(s)".

Claim 16, Column 28, line 12, after "claim" insert --1--.

Claim 17, Column 28, line 23, delete "tai" and insert --the fatty--.

Signed and Sealed this
Fifth Day of May, 2015

Michelle K. Lee
*Director of the United States Patent and Trademark Office*